United States Patent [19]

Föry et al.

[11] Patent Number: 5,352,654
[45] Date of Patent: Oct. 4, 1994

[54] PYRIDYL SULFONYLUREA HERBICIDES

[75] Inventors: Werner Föry, Riehen; Rolf Schurter, Binningen, both of Switzerland

[73] Assignee: Ciba-Geigy Corporation, Ardsley, N.Y.

[21] Appl. No.: 530,690

[22] Filed: May 30, 1990

[30] Foreign Application Priority Data

Jun. 6, 1989 [CH] Switzerland ............ 2135/89-2
Jul. 18, 1989 [CH] Switzerland ............ 2679/89-9

[51] Int. Cl.$^5$ ............ A01N 43/66; A01N 43/54; C07D 251/46
[52] U.S. Cl. ............ 504/230; 504/239; 544/216; 544/331
[58] Field of Search ............ 544/331, 216; 71/92, 71/93; 504/230, 239

[56] References Cited

U.S. PATENT DOCUMENTS

| | | | |
|---|---|---|---|
| 4,456,469 | 6/1984 | Adams, Jr. et al. | 544/209 |
| 4,579,583 | 4/1986 | Föry | 71/92 |
| 4,713,109 | 12/1987 | Schuster et al. | 71/94 |
| 4,774,337 | 9/1988 | Liang | 546/293 |

FOREIGN PATENT DOCUMENTS

| | | |
|---|---|---|
| 0103543 | 3/1984 | European Pat. Off. |
| 2832977 | 2/1980 | Fed. Rep. of Germany |
| 8113791 | 7/1981 | France |

OTHER PUBLICATIONS

Liang, Paul Hsiao Tseng, Chemical Abstract vol. 109, 1988 entery #230861u.
J. Am. Chem. Soc. 72, 1687 (1950).
Advances in Aeterocyclic Chemistry 6 (1966).
Organic Synthesis, vol. 35 65-69, 1955.
Journal of Fluorine Chemistry, 21 (1982) 171-189.
Can. J. Chem. 57 (1979).
Federick Leonard (1954) pp. 2855-2860, vol. 77 J. Am. Chem. Soc. 77 (1955).

*Primary Examiner*—Mukund J. Shah
*Assistant Examiner*—Y. N. Gupta
*Attorney, Agent, or Firm*—Kevin T. Mansfield; Edward McC. Roberts

[57] ABSTRACT

N-Pyridinesulfonyl-N'-pyrimidinyl- and -triazinylureas of the formula I

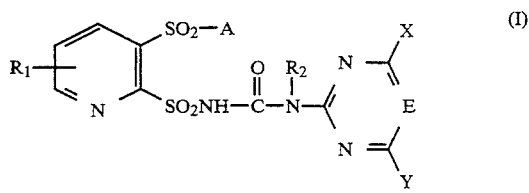

in which $R_1$ is hydrogen, halogen, $C_1$-$C_4$alkyl, $C_1$-$C_4$alkoxy, $C_1$-$C_4$alkylthio, $C_1$C_4$haloalkoxy or $CF_3$; $R_2$ is hydrogen or $C_1$-$C_4$alkyl; A is $C_1$-$C_6$alkyl or $C_3$-$C_6$cycloalkyl, each of which is monosubstituted to trisubstituted by halogen, or is $C_1$-$C_4$alkyl or $C_3$-$C_6$cycloalkyl, each of which is substituted by $C_1$-$C_4$alkoxy, $C_1$-$C_4$alkylthio, $C_1$-$C_4$alkylsulfonyl, $C_1$-$C_4$alkylsulfinyl, $C_2$-$C_4$alkenyl, $C_5$-$C_6$cycloalkenyl, amino, $C_1$-$C_4$alkylamino, $C_1$-$C_4$dialkylamino or $C_2$-$C_4$alkynyl, it being possible for the $C_2$-$C_4$alkenyl radical and the $C_5$-$C_6$cycloalkenyl radical to be additionally monosubstituted to trisubstituted by halogen; or A is a 4- to 6-membered saturated heterocycle which contains a hetero atom selected from the group comprising O, N and $SO_2$; or A is $C_1$-$C_4$alkyl which is substituted by a 4- to 6-membered saturated heterocycle which contains a hetero atom selected from the group comprising O, N and $SO_2$; X is $C_1$-$C_3$alkyl, $C_1$-$C_3$alkyl which is monosubstituted to trisubstituted by halogen, or is $C_1$-$C_3$alkoxy or $C_1$-$C_3$alkoxy which is monosubstituted to trisubstituted by halogen; Y is halogen, $C_1$-$C_3$alkyl, $C_1$-$C_3$alkyl which is monosubstituted to trisubstituted by halogen, or is $C_1$-$C_3$alkoxy, $C_1$-$C_3$alkoxy which is monosubstituted to trisubstituted by halogen, or is cyclopropyl, methylamino or dimethylamino; and E is nitrogen or the methine group, and the salts of these compounds with amines, alkali metal bases or alkaline earth metal bases or with quaternary ammonium bases have good selective herbicidal properties pre-emergence and post-emergence, and good growth-regulating properties.

23 Claims, No Drawings

PYRIDYL SULFONYLUREA HERBICIDES

The present invention relates to novel herbicidally active and plant growth-regulating N-pyridinesulfonyl-N'-pyrimidinyl- and -triazinylureas, to processes for their preparation, to compositions containing them as active substances, and to their use for controlling weeds, mainly selectively in crops, or for regulating and inhibiting plant growth.

Urea compounds, triazine compounds and pyrimidine compounds which have a herbicidal action are generally known. For example, European Patent No. 103,543 describes herbicidally active and plant growth-regulating N-pyridinesulfonyl-N'-pyrimidinyl- and- triazinylureas. However, the active substances disclosed in this patent cannot always meet the requirements with regard to effectiveness and selectivity. There is therefore a demand for more effective and more selective active substances.

Novel sulfonylureas which have improved herbicidal and plant growth-regulating properties have now been found.

The N-pyridinesulfonyl-N'-pyrimidinyl- and- triazinylureas according to the invention are those of the formula I

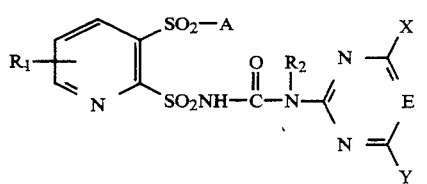

in which $R_1$ is hydrogen, halogen, $C_1$–$C_4$alkyl, $C_1$–$C_4$alkoxy, $C_1$–$C_4$alkylthio, $C_1$–$C_4$haloalkoxy or $CF_3$; $R_2$ is hydrogen or $C_1$–$C_4$alkyl; A is $C_1$–$C_6$alkyl or $C_3$–$C_6$cycloalkyl, each of which is monosubstituted to trisubstituted by halogen, or is $C_1$–$C_4$alkyl or $C_3$–$C_6$cycloalkyl, each of which is substituted by $C_1$–$C_4$alkoxy, $C_1$–$C_4$alkylthio, $C_1$–$C_4$alkylsulfonyl, $C_1$–$C_4$alkylsulfinyl, $C_2$–$C_4$alkenyl, $C_5$–$C_6$cycloalkenyl, amino, $C_1$–$C_4$alkylamino, $C_1$–$C_4$dialkylamino or $C_2$–$C_4$alkynyl, it being possible for the $C_2$–$C_4$alkenyl radical and the $C_5$–$C_6$cycloalkenyl radical to be additionally monosubstituted to trisubstituted by halogen; or A is a 4- to 6-membered saturated heterocycle which contains a hetero atom selected from the group comprising O, N and $SO_2$; or A is $C_1$–$C_4$alkyl which is substituted by a 4- to 6-membered saturated heterocycle which contains a hetero atom selected from the group comprising O, N and $SO_2$; X is $C_1$–$C_3$alkyl, $C_1$–$C_3$alkyl which is monosubstituted to trisubstituted by halogen, or is $C_1$–$C_3$alkoxy or $C_1$–$C_3$alkoxy which is monosubstituted to trisubstituted by halogen; Y is halogen, $C_1$–$C_3$alkyl, $C_1$–$C_3$alkyl which is monosubstituted to trisubstituted by halogen, or is $C_1$–$C_3$alkoxy, $C_1$–$C_3$alkoxy which is monosubstituted to trisubstituted by halogen, or is cyclopropyl, methylamino or dimethylamino; and E is nitrogen or the methine group, and the salts of these compounds.

The $C_1$–$C_4$alkyl groups which occur as, or in the, substituents $R_1$, $R_2$ and A can be straight-chain or branched and specifically comprise methyl, ethyl, n-propyl, iso-propyl, n-butyl, sec-butyl, iso-butyl and tert-butyl. The alkyl groups which are present as, or in the, substituents $R_1$, $R_2$ and A preferably have one to three carbon atoms. Methyl is particularly preferred for the substituents $R_1$ and $R_2$.

Examples of haloalkoxy are fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy; difluoromethoxy, 2-chloroethoxy and trifluoromethoxy are preferred.

The substituent A, as a $C_1$–$C_6$alkyl group which is monosubstituted to trisubstituted by halogen, comprises straight-chain or branched alkyl groups, such as methyl, ethyl, n-propyl, iso-propyl, n-butyl, sec-butyl, iso-butyl, tert-butyl, n-pentyl, the pentyl isomers, n-hexyl and the hexyl isomers, each of which is monosubstituted to trisubstituted by halogen, halogen specifically being fluorine, chlorine, bromine or iodine.

From amongst these $C_1$–$C_6$alkyl groups which are monosubstituted to trisubstituted by halogen, $C_1$–$C_4$alkyl groups which are monosubstituted to trisubstituted by halogen are preferred. Preferred halogen atoms which can occur as substituents of the $C_2$–$C_6$alkyl groups are fluorine and chlorine. Especially preferred alkyl groups which are monosubstituted to trisubstituted by halogen are trifluoromethyl, 1-fluoroethyl, 1,1-dichloroethyl, 3,3,3-trifluoropropyl, 2-fluoroisopropyl, 3-fluoropropyl, 1,1,1-trichloropentyl, 1-fluoro-3-methylpentyl or 1-bromohexyl. 3-Fluoropropyl and 2-fluoroisopropyl are very particularly preferred.

The $C_2$–$C_4$alkenyl radicals which occur in the substituent A can be in the Z-form (cis) or in the E-form (trans) and can be straight-chain or branched. Alkenyl radicals which have a chain length of two to three carbon atoms are preferred. The following are examples of $C_2$–$C_4$alkenyl radicals: vinyl, allyl, methallyl, 1-methylvinyl and but-2-en-1-yl. Vinyl and allyl are preferred. In the $C_2$–$C_4$alkenyl radicals which are monosubstituted to trisubstituted by halogen, halogen specifically represents fluorine, chlorine, bromine and iodine. Preferred halogen atoms which can occur as substituents of the $C_2$–$C_4$alkenyl radicals are fluorine and chlorine. Preferred radicals from amongst the $C_2$–$C_4$alkenyl radicals which are monosubstituted to trisubstituted by halogen are those which have a chain length of two to three carbon atoms. $C_2$–$C_4$Alkenyl radicals which are monosubstituted to trisubstituted by halogen and which are especially preferred are 1-chlorovinyl, 2-chlorovinyl, 3-fluoroallyl and ,4,,4,,4-trifluorobut-2-en-1-yl. 1-Chlorovinyl and 2-chlorovinyl are very particularly preferred.

The $C_2$–$C_4$alkynyl radicals which occur in the definitions of the substituent A can be straight-chain or branched. Preferred alkynyl radicals are those which have a chain length of two to three carbon atoms. Examples of $C_2$–$C_4$alkynyl radicals are ethynyl, propargyl, 1-propynyl, 3-butynyl or 1-methylpropargyl, ethynyl and propargyl being particularly preferred.

The $C_3$–$C_6$cycloalkyl groups which are monosubstituted to trisubstituted by halogen and which occur in substituent A comprise, for example, 2-fluorocyclopropyl, 2,3-difluorocyclopropyl, 2,2-dichlorocyclopropyl, 3-bromocyclopropyl, 2,3,4-trifluorocyclopentyl or 2,3-dichlorocyclohexyl. Preferred amongst these $C_3$–$C_6$cycloalkyl groups are the cyclopropyl, cyclopentyl and cyclohexyl groups which are monosubstituted to disubstituted by halogen, halogen being fluorine, chlorine, bromine and iodine, but in particular fluorine and chlorine.

Examples of other substituted $C_3C_6$cycloalkyl groups are 2-methoxycyclopropyl, 3-ethylthiocyclobutyl, 2-methylsulfonylcyclopentyl, 3-ethylsulfinylcyclohexyl, 4-allylcyclohexyl or 3-propargylcyclohexyl.

The $C_5$-$C_6$cycloalkenyl radicals can be monosubstituted to trisubstituted by halogen. Preferred halogen atoms in this context are fluorine and chlorine. Examples of $C_5$-$C_6$cycloalkenyl radicals are 3-cyclopentene, 2-cyclopentene, 4-chlorocyclopent-3-ene, 3,4-difiuorocyclopent-3-ene, 2-cyclohexene, 3-cyclohexene, 4,5-dibromocyclohex-2-ene or 4,4,5-trifluorocyclohex-2-ene.

Examples of saturated 4- to 6-membered heterocycles are oxetan-3-yl, oxolan-2-yl, oxan-2-yl, azetidin-3-yl, azolidin-3-yl, perhydroazin-4-yl (piperidin-4-yl), dioxothiolan-2-yl, dioxothiethan-3-yl or dioxothian-4-yl. The nitrogen atom in the heterocycle can also be substituted by $C_1$-$C_4$alkyl, for example in N-methylperhydroazin-4-yl or N-isopropylazolidin-2-yl.

The $C_1$-$C_3$alkyl radicals which occur as, or in the definitions of, the substituents X and Y specifically comprise methyl, ethyl, n-propyl and iso-propyl as well as the haloalkyls which are derived from these radicals and which are monosubstituted to trisubstituted by halogen. The alkyl radicals which occur as, or in the definitions of the substituents, X and Y preferably have one to two carbon atoms.

Groups which are preferred in the $C_1$-$C_3$alkyl groups which are monosubstituted to trisubstituted by halogen and which occur as, or in the definitions of, the substituents X and Y are $C_1$-$C_2$alkyl groups which are monosubstituted to trisubstituted by fluorine or chlorine. Especially preferred $C_1$-$C_3$alkyl radicals which are monosubstituted to trisubstituted by halogen are trifluoromethyl, difluoromethyl, 2-chloroethyl, chlorodifluoromethyl, dichloromethyl, chlorofluoromethyl, 1,1-dichloroethyl, trifluoroethyl, 3,3,3-trifluoropropyl or 2,3-dichloropropyl, and fluoromethyl, chloromethyl, difluoromethyl and trifluoromethyl are particularly preferred.

The invention likewise comprises salts which can be formed by the compounds of the formula I with amines, alkali metal bases, alkaline earth metal bases or quaternary ammonium bases.

Compounds which must be emphasized as salt formers from amongst the alkali metal hydroxides and alkaline earth metal hydroxides are the hydroxides of lithium, sodium, potassium, magnesium or calcium, but in particular those of sodium or potassium.

Examples of amines which are suitable for salt formation are primary, secondary and tertiary aliphatic and aromatic amines, such as methylamine, ethylamine, propylamine, iso-propylamine, the four butylamine isomers, dimethylamine, diethylamine, diethanolaniine, dipropylamine, diisopropylamine, di-n-butylamine, pyrrolidine, piperidine, morpholine, trimethylamine, triethylamine, tripropylamine, quinuclidine, pyridine, quinoline and iso-quinoline, but in particular ethylamine, propylamine, diethylamine or triethylamine, but especially iso-propylamine and diethanolamine.

Examples of quaternary ammonium bases are, in general, the cations of haloammonium salts, for example the tetramethylammonium cation, the trimethylbenzylammonium cation, the triethylbenzylammonium cation, the tetraethylammonium cation, the trimethylethylammonium cation, but also the ammonium cation.

Preferred amongst the compounds of the formula I are those in which $R_1$ is hydrogen, halogen, $C_1$-$C_4$alkyl, $C_1$-$C_4$alkoxy, $C_1$-$_4$alkylthio or $CF_3$; $R_2$ is hydrogen or $C_1$-$C_4$alkyl; A is $C_2$-$C_6$alkyl which is monosubstituted to trisubstituted by halogen; or A is $C_1$-$C_4$alkyl which is substituted by $C_1$-$C_4$alkoxy, $C_1$-$C_4$alkylthio, $C_1$-$C_4$alkylsulfonyl, $C_1$-$C_4$alkylsulfinyl, $C_2$-$C_4$alkenyl or $C_2$-$C_4$alkynyl, it being possible for the $C_2$-$C_4$alkenyl radical to be additionally monosubstituted to trisubstituted by halogen; X is $C_1$-$C_3$alkyl or $C_1$-$C_3$alkyl which is monosubstituted to trisubstituted by halogen, or is $C_1$-$C_3$alkoxy or $C_1$-$C_3$alkoxy which is monosubstituted to trisubstituted by halogen; Y is halogen, $C_1$-$C_3$alkyl, $C_1$-$C_3$alkyl which is monosubstituted to trisubstituted by halogen, or is $C_1$-$C_3$alkoxy, $C_1$-$C_3$alkoxy which is monosubstituted to trisubstituted by halogen, or is cyclopropyl, methylamino or dimethylamino; and E is nitrogen or the methine group.

Furthermore preferred compounds amongst those of the formula I are those in which
a) $R_2$ is hydrogen;
b) $R_1$ and $R_2$ are hydrogen;
c) $R_1$ is hydrogen, methyl, methoxy, fluorine or chlorine;
d) X is $C_1$-$C_3$alkyl, $C_1$-$C_3$alkoxy or alkoxy which is monosubstituted to trisubstituted by halogen; and Y is $C_1$-$C_3$alkyl, $C_1$-$C_3$alkoxy, $C_1$-$C_3$alkoxy which is monosubstituted to trisubstituted by halogen, or is chlorine;
e) A is $C_1$-$C_6$alkyl or $C_3$-$C_6$cycloalkyl, each of which is monosubstituted to trisubstituted by halogen; or A is $C_1$-$C_4$alkyl or $C_3$-$C_6$cycloalkyl, each of which is substituted by $C_1$-$C_4$alkoxy, $C_5$-$C_6$cycloalkenyl or $C_2$-$C_4$alkenyl; it being possible for the $C_2$-$C_4$alkenyl radical and for the $C_5$-$C_6$cycloalkenyl radical to be additionally monosubstituted to trisubstituted by halogen.

From amongst these compounds, those in which
a) A is allyl, methallyl, 3-chloroallyl, methoxyethyl, 2-fluoroisopropyl or 3-fluoropropyl;
b) $R_1$ and $R_2$ are hydrogen;
c) X is methyl, methoxy, ethoxy or difluoromethoxy and Y is methyl, methoxy, ethoxy, difluoromethoxy or chlorine,
must be particularly emphasized.

A preferred sub-group of compounds of the formula I which must be emphasized is the group in which $R_1$ is hydrogen, halogen, $C_1$-$C_2$alkyl, $C_1$-$C_2$alkoxy, $C_1$-$C_2$alkylthio, $C_1$-$C_2$-haloalkoxy or $CF_3$; $R_2$ is hydrogen or $C_1$-$C_2$alkyl; A is $C_1$-$C_4$alkyl or $C_3$-$C_6$cycloalkyl, each of which is monosubstituted to trisubstituted by halogen, or is $C_1$-$C_2$alkyl or $C_3$-$C_6$cycloalkyl, each of which is substituted by $C_1$-$C_2$alkoxy, $C_1$-$C_2$alkylthio, $C_1$-$C_2$alkylsulfonyl, $C_1$-$C_2$alkylsulfinyl, $C_2$-$C_3$alkenyl, $C_5$-$C_6$cycloalkenyl, amino, $CFC_2$alkylamino, $C_1$-$C_4$-dialkylamino or $C_2$-$C_3$alkynyl, it being possible for the $C_2$-$C_3$alkenyl radical and for the $C_5$-$C_6$cycloalkenyl radical to be additionally monosubstituted to trisubstituted by halogen; or A is a 4- to 6-membered saturated heterocycle which contains a hetero atom selected from the group comprising O, N and $SO_2$; or A is $C_1$-$C_2$alkyl which is substituted by a 4- to 6-membered saturated heterocycle which contains a hetero atom selected from the group comprising O, N and $SO_2$; X is $C_1$-$C_2$alkyl, $C_1$-$C_2$alkyl which is monosubstituted to trisubstituted by halogen, or is $C_1$-$C_2$alkoxy or $C_1$-$C_2$alkoxy which is monosubstituted to trisubstituted by halogen; Y is halogen, $C_1$-$C_2$alkyl, $C_1$-$C_2$alkyl which is monosubstituted to trisubstituted by halogen, or is $C_1$-$C_2$alkoxy, $C_1$-$C_2$alkoxy which is monosubstituted to trisubstituted by halogen, or is cyclopropyl, methylamino or dimethylamino.

In a further sub-group of compounds of the formula I, $R_1$ is hydrogen, halogen, $C_1$-$C_2$alkyl, $C_1$-$C_2$alkylthio or $CF_3$; $R_2$ is hydrogen or $C_1$-$C_2$alkyl; A is $C_2$-$C_4$alkyl whi is monosubstituted to trisubstituted by halogen or is $C_1$-$C_2$alkyl which is substituted by $C_1$-$C_2$alkoxy, $C_1$-$C_2$alkylthio, $C_1$-$C_2$alkylsulfonyl, $C_1C_2$alkylsulfinyl, $C_2$-$C_3$alkenyl or $C_2$-$C_3$alkynyl, it being possible for the $C_2$-$C_3$alkenyl radical to be additionally monosubstituted to trisubstituted by halogen; X is $C_1$-$C_2$alkyl, $C_1$-$C_2$alkyl which is monosubstituted to trisubstituted by halogen, or is $C_1$-$C_2$alkoxy or $C_1$-$C_2$alkoxy which is monosubstituted to trisubstituted by halogen; Y is halogen, $C_1$-$C_2$alkyl, $C_1$-$C_2$alkyl which is monosubstituted to trisubstituted by halogen, or is $C_1$-$C_2$alkoxy, $C_1$-$C_2$alkoxy which is monosubstituted to trisubstituted by halogen, or is cyclopropyl, methylamino or dimethylamino.

The group in which $R_1$ and $R_2$ are hydrogen; A is $C_1$-$C_4$alkyl which is monosubstituted to trisubstituted by halogen, or is $C_1$-$C_2$alkyl or $C_3$-$C_6$cycloalkyl, each of which is substituted by $C_1$-$C_4$alkoxy, $C_5$-$C_6$cycloalkenyl or $C_1$-$C_2$alkenyl, it being possible for the $C_2$-$C_3$alkenyl radical and for the $C_5$-$C_6$cycloalkenyl radical to be additionally monosubstituted to trisubstituted by fluorine or chlorine, must be emphasized as another preferred sub-group of compounds of the formula I.

Compounds from this group which are particularly conspicuous because of their good biological action are those in which A is allyl, methallyl, 3-chloroallyl, methoxyethyl, 2-fluoroisopropyl or 3-fluoropropyl; X is methyl, methoxy, ethoxy or difluoromethoxy, Y is methyl, methoxy, ethoxy, difluoromethoxy or chlorine, and E is the methine group.

Preferred individual compounds from the scope of the formula I which must be mentioned are: N-(3-allylsulfonylpyridin-2-ylsulfonyl)-N'-(4,6-dimethoxypyrimidin-2-yl)urea, N-(3-methoxyethylsulfonylpyridin-2-ylsulfonyl)-N'-(4,6-dimethoxypyrimidin-2-yl)urea, N-(3-fluoropropylsulfonylpyridin-2-ylsulfonyl)-N'-(4,6-dimethoxypyrimidin-2-yl)urea and N-(3-methallylsulfonylpyridin-2-ylsulfonyl)-N'-(4,6-dimethoxypyrimidin-2-yl)urea.

According to a first process, the compounds of the formula I can be prepared by reacting a pyridylsulfonamide of the formula II

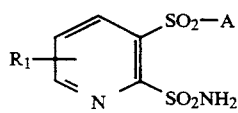

(II)

in which $R_1$ and A are as defined under formula I, with the proviso that A cannot be α-haloalkyl or α-halocycloalkyl, with an N-pyrimidinyl carbamate or N-triazinyl carbamate of the formula IV

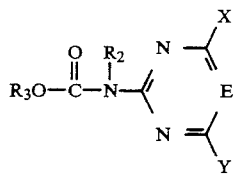

(IV)

in which X, Y, $R_2$ and E are as defined under formula I, and $R_3$ is $C_1$-$C_4$alkyl or phenyl which can be substituted by $C_1$-$C_4$alkyl or halogen, in the presence of a base.

According to a second process, the compounds of the formula I can be prepared by reacting a pyridylsulfonamide of the formula II

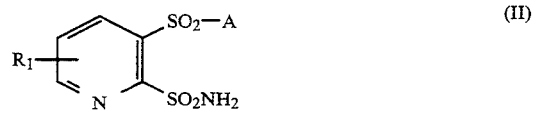

(II)

in which $R_1$ and A are as defined under formula I, with a pyrimidinyl isocyanate or triazinyl isocyanate of the formula VIII

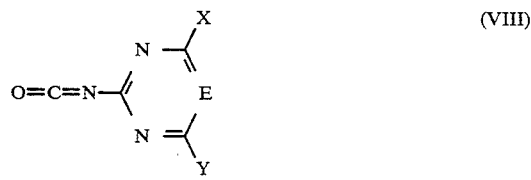

(VIII)

in which E, X and Y are as defined under formula I, in the presence of a base.

According to a third process, the compounds of the formula I can be prepared by oxidizing, by processes known per se, compounds of the formula XVI

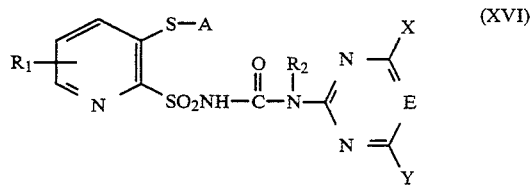

(XVI)

which are known from European Patent No. 103,543 and in which $R_1$, $R_2$, A, E, X and Y are as defined under formula I.

Oxidations of thio compounds to give the corresponding sulfonyl compounds are described in U.S. Pat. No. 4,774,337. Oxidants which are suitable for this reaction are, for example, peracids or hydrogen peroxide. If desired, the resulting ureas of the formula I can be converted into salts by means of amines, alkali metal hydroxides, alkaline earth metal hydroxides or quaternary ammonium bases. This is carded out, for example, by reacting them with the equimolar amount of base and evaporating the solvent.

The reactions to give compounds of the formula I are carded out advantageously in aprotic, inert organic solvents. Such solvents are hydrocarbons, such as benzene, toluene, xylene or cyclohexane, chlorinated hydrocarbons, such as dichloromethane, trichloromethane, tetrachloromethane or chlorobenzene, ethers, such as diethyl ether, ethylene glycol dimethyl ether, diethylene glycol dimethyl ether, tetrahydrofuran or dioxane, nitriles, such as acetonitrile or propionitrile, or amides, such as dimethylformamide, diethylformamide or N-methylpyrrolidinone. The reaction temperatures are preferably between −20° and +120° C. In general, the reactions proceed slightly exothermally and can be carried out at room temperature. To shorten the reaction time, or else to initiate the reaction, it is expedient to heat the reaction mixture briefly to the boiling point.

It is also possible to shorten the reaction times by adding a few drops of base as reaction catalyst. Suitable bases are, in particular, tertiary amines, such as trimethylamine, triethylamine, quinuclidine, 1,4-diazabicyclo(2.2.2)octane, 1,5-diazabicyclo(4.3.0)non-5-ene or 1,5-diazabicyclo(5.4.0)undec-7-ene. However, bases which can also be used are inorganic bases, such as hydrides, such as sodium hydride or calcium hydride, hydroxides, such as sodium hydroxide and potassium hydroxide, carbonates, such as sodium carbonate and potassium carbonate, or hydrogen carbonates, such as potassium hydrogen carbonate and sodium hydrogen carbonate.

The end products of the formula I can be isolated by concentration and/or evaporation of the solvent, and they can be purified by recrystallization or trituration of the solid residue in solvents in which they are not readily soluble, such as ethers, aromatic hydrocarbons or chlorinated hydrocarbons.

The intermediates of the formula II are novel and were developed specifically for the synthesis of the compounds of the formula I. They form therefore a part of the present invention.

The novel intermediates of the formula II can be prepared by various processes. For example, the compounds of the formula IIc

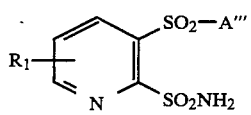
(IIc)

in which $R_1$ is as defined under formula I and A''' is $C_1$-$C_4$alkyl or $C_3$-$C_6$cycloalkyl, each of which is substituted by $C_2$-$C_4$alkenyl, $C_5$-$C_6$cycloalkenyl, $C_2$-$C_4$alkynyl, $C_1$-$C_4$alkoxy, $C_1$-$C_4$alkylthio, $C_1$-$C_4$alkylsulfonyl or $C_1$-$C_4$alkylsulfinyl, or is $C_1$-$C_6$alkyl or $C_3$-$C_6$cycloalkyl, each of which is substituted by fluorine, are obtained by reacting a 3-fluoropyridin-2-ylsulfonamide of the formula IIIa

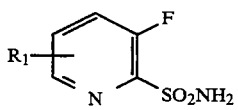
(IIIa)

in which $R_1$ is as defined under formula I, with a mercaptan of the formula V

   (V)

in which A''' is as defined under formula IIc, in the presence of a base, and subsequently oxidizing the resulting compound of the formula VI

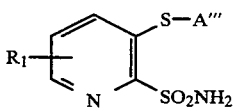
(VI)

in which $R_1$ is as defined under formula I and A''' is as defined under formula IIc, by processes known per se, to give the compound of the formula IIc.

Intermediates of the formula II

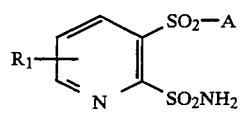
(II)

in which $R_1$ and A are as defined under formula I are also obtained by reacting a 3-mercaptopyridin-2-ylsulfonamide of the formula IIIb

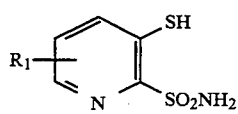
(IIIb)

in which $R_1$ is as defined under formula I, with a compound of the formula XVIII

Z—A   (XVIII)

in which A is as defined under formula I and Z is chlorine, bromine, iodine, $CH_3SO_2O$— or

in the presence of a base to give the compound of the formula XX

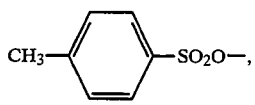
(XX)

in which A is as defined under formula I, and subsequently oxidizing this compound to give the compound of the formula II. The intermediates of the formula III

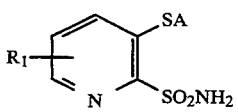
(III)

in which $R_1$ is as defined under formula I and Q is fluorine or —SH are novel with the exeption of the compound in which $R_1$ is hydrogen and Q is —SH and likewise a subject of the present invention. The scope of the formula HI also includes the compounds of the sub-formulae IIIa and IIIb.

The compounds of the formulae IIIa and IIIb can be prepared by methods known per se by reacting, in the case of the compound of the formula IIIa, a 2,3-difluoropyridine of the formula IX

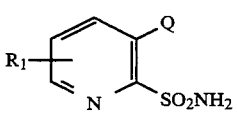
(IX)

in which $R_1$ is as defined under formula I, with a mercaptan of the formula X

R₄SH                                                              (X)

in which R₄ is benzyl or iso-propyl, to give a compound of the formula XI

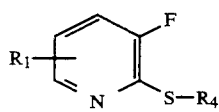                                                              (XI)

in which R₁ is as defined under formula I and R₄ is benzyl or iso-propyl, to subsequently obtain the compound of the formula IIIa by chlorination with chlorine gas and reaction with ammonia.

Compounds of the formula IIIa can also be prepared by diazotizing a 3-aminopyridin-2-ylsulfonamide of the formula XXI

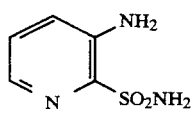                                                              (XXI)

with a nitrite, in the presence of hydrogen fluoride and if desired in the presence of an inert solvent.

Examples of suitable nitrites are sodium nitrite or potassium nitrite, and dimethyl sulfoxide, sulfolane, dimethylformamide or dimethylacetamide are particularly suitable as solvents. Intermediates of the formula IIIb are prepared by reacting a 3-fluoropyridin-2-ylsulfonamide of the formula IIIa with a mercaptide of the formula XIX (Me)ₙH₂₋ₙSⁿ                                                       (XIX)

in which Ma is sodium, potassium or lithium and n is 1 or 2.

Processes for the preparation of the compounds of the formula IX are found, for example, in J. Fluorine Chem. 21, 171 (1982) (R₁=H); U.S. Pat. No. 4,713,109 (R₁=Cl) or in Advanc. Heterocycl. Chem. 6, 229 (1966).

Compounds of the sub-formula IIa

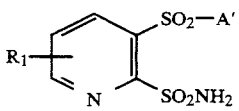                                                              (IIa)

in which R₁ is as defined under formula I and A' is C₁-C₆alkyl or C₃-C₆cycloalkyl, each of which is substituted by fluorine, or is C₁-C₄alkyl or C₃-C₆cycloalkyl, each of which is substituted by C₁-C₄alkoxy or C₁-C₄alkylthio, can also be prepared, in analogy with a process described in U.S. Pat. No. 4,774,337, by reacting a compound of the formula XII

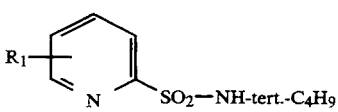                                                              (XII)

in which R₁ is as defined under formula I, with a disulfide of the formula XIII

'A—S—S—A'                                                        (XIII)

in which A' is as defined under formula IIa, in the presence of a strong base, for example n-butyllithium or lithium diisopropylamide, treating the resulting compound of the formula XIV

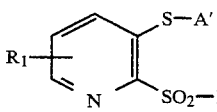                                                              (XIV)

in which R₁ is as defined under formula I and A' is as defined under formula IIa, with a suitable acid, for example trifluoroacetic acid, and subsequently oxidizing the resulting sulfonamide of the formula XV

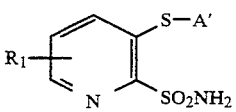                                                              (XV)

in which R₁ is as defined under formula I and A' is as defined under formula IIa, to give the compound of the formula II.

The intermediates of the sub-formula IIb

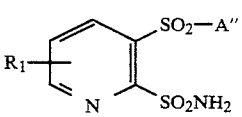                                                              (IIb)

in which R₁ is as defined under formula I and A″ is C₂-C₄alkyl which is substituted by fluorine, chlorine or bromine, are furthermore obtained by converting a hydroxysulfonamide of the formula XVII

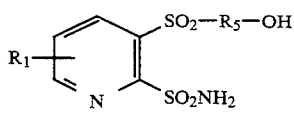                                                              (XVII)

in which R₁ is as defined under formula I and R₅ is C₂-C₄alkylene, into the corresponding halides. Such reactions are described, for example, in Can. J. Chem. 57, 3193 (1979) or in French Patent Specification No. 2,509,725.

The mercaptans of the formulae V and X and the disulfide of the formula XIII are prepared by methods known from the literature. The following may be mentioned as representatives from the large number of published articles: DE 2,832,977; J. Am. Chem. Soc. 77,2855 (1955); J. Am. Chem. Soc. 72, 1687 (1950) and Org. Synth. 35, 66 (1955).

The active substances of the formula I are generally successfully employed at application rates of 0.001 to 5 kg/ha, in particular 0.005 to 3 kg/ha. The dosage rate required for the desired effect can be determined by experiments. It depends on the nature of the effect, the development stage of the crop plant and the weed and on the application (location, time, method) and, as a function of these parameters, can vary within wide limits.

At low application rates, the compounds of the formula I are distinguished by growth-inhibiting and herbicidal properties, which makes them outstandingly suitable for use in crops, in particular in cereals, cotton, soybean, oilseed rape, maize and rice, the use in maize crops being very particularly preferred.

The invention also relates to herbicidal and plant growth- regulating compositions which contain a novel active substance of the formula I and to methods for inhibiting plant growth.

Plant growth regulators are substances which cause agronomically desirable biochemical and/or physiological and/or morphological modifications in/on the plant.

The active substances contained in the compositions according to the invention affect plant growth in many ways, depending on the point in time of application, the dosage rate, the type of application and the prevailing environment. For example, plant growth regulators of the formula I can inhibit the vegetative growth of plants. This type of action is of interest on lawns, in the production of ornamental plants, in orchards, on verges, on sports grounds and industrial terrain, but also in the targeted inhibition of secondary shoots, such as in tobacco. In arable farming, inhibition of the vegetative growth in cereals by strengthening the stem results in reduced lodging, and similar agronomical effects are achieved in oilseed rape, sunflowers, maize and other crop plants. Furthermore, inhibition of the vegetative growth means that the number of plants per unit area can be increased. Another field in which growth inhibitors can be applied is the selective control of ground-cover plants, in plantations or crops with plenty of space between the rows, by powerful growth inhibition without destroying these cover crops, so that competition with the main crop is eliminated, but the agronomically positive effects, such as reduction of erosion, nitrogen fixation and loosening of the soil, are retained.

A method for inhibiting plant growth is understood as meaning controlling the natural development of the plant without altering the life cycle of the plant, which is determined by its genetic make-up, in the sense of a mutation. The method of growth regulation is applied at a particular point in time of the development of the plant, which is to be determined in the particular case. The active substances of the formula I can be applied before or after emergence of the plants, for example already to the seeds or seedlings, to roots, tubers, stalks, leaves, flowers or other parts of the plants. This can be effected, for example, by applying the active substance, as such or in the form of a composition, to the plants and/or by treating the nutrient substrate of the plant (soil).

Various methods and techniques are suitable for using the compound of the formula I or compositions containing it for regulating plant growth, for example the following:

i) Seed treatment a) The seeds are treated with an active substance formulated as a wettable powder by shaking in a container until the seed surface is uniformly covered (dry seed treatment). Up to 4 g of active substance of the formula I are used per kg of seed in this method (up to 8.0 of wettable powder in the case of a 50 % formulation).

b) Treating the seeds with an emulsion concentrate of the active substance or with an aqueous solution of the active substance of the formula I formulated as a wettable powder, using method a) (wet seed treatment).

c) Seed treatment by immersing the seeds in a liquor containing up to 1000 ppm of active substance of the formula I for 1 to 72 hours, which, if desired, is followed by drying the seeds (seed soaking).

Naturally, seed treatment or treatment of the germinated seedling are the preferred application methods since the treatment with active substance is directed entirely at the target crop. 4.0 g to 0.001 g of active compound are generally used per kg of seed, but it is possible to deviate from the limit concentrations given in both directions, depending on the method chosen which also makes possible the addition of other active substances or micronutrients (repeated seed treatment).

ii) Controlled release of active substance

The dissolved active substance is applied to mineral granule carriers or polymerized granules (urea/formaldehyde) and allowed to dry. If desired, a coating can be applied (coated granules), which permits slow release of the active substance over a certain period.

The compounds of the formula I are employed in unaltered form, or preferably as compositions, together with the auxiliaries conventionally used in the art of formulation, and they are therefore processed in a known manner to give, for example, emulsion concentrates, directly sprayable or dilutable solutions, dilute emulsions, wettable powders, soluble powders, dusts, granules, and also encapsulations, for example in polymeric substances. The application methods, such as spraying, misting, atomizing, scattering or pouring, as well as the kind of compositions are selected to suit the intended aims and the prevailing circumstances.

The formulations, i.e. the compositions, preparations or combinations containing the active substance of the formula I and, if desired, a solid or liquid additive, are prepared in a known manner, for example by intimately mixing and/or grinding the active substances with extenders, for example with solvents, solid carriers and, if desired, surface-active compounds (surfactants).

The following are possible as solvents: aromatic hydrocarbons, preferably the fractions $C_8$ to $C_{12}$, for example xylene mixtures or substituted naphthalenes, phthalic esters, such as dibutyl phthalate or dioctyl phthalate, aliphatic hydrocarbons, such as cyclohexane, paraffins, alcohols and glycols as well as their ethers and esters, such as ethanol, ethylene glycol, ethylene glycol monomethyl ether or ethylene glycol monoethyl ether, ketones, such as cyclohexanone, strongly polar solvents, such as N-methyl-2-pyrrolidone, dimethyl sulfoxide or dimethylformamide, and also epoxidized or unepoxidized vegetable oils, such as epoxidized coconut oil or soya oil; or water.

Solid carders which are generally used, for example for dusts and dispersible powders, are ground natural minerals, such as calcite, talc, kaolin, montmorillonite or attapulgite. To improve the physical properties, it is also possible to add highly-disperse silicas or highly-disperse absorptive polymers. Possible particulate, adsorptive carriers for granules are either porous types, for example pumice, brick grit, sepiolite or bentonite, or non-sorptive carrier materials, such as calcite or sand. Moreover, a large number of pregranulated materials of inorganic or organic nature can be used, such as, in particular, dolomite or comminuted plant residues.

Suitable surface-active compounds are non-ionic, cationic and/or anionic surfactants having good emulsifying, dispersing and wetting properties, depending on the nature of the active substance of the formula I to be formulated. Surfactants are also to be understood as meaning mixtures of surfactants.

Anionic surfactants which are suitable can be either so-called water-soluble soaps or water-soluble synthetic surface-active compounds.

Suitable soaps which may be mentioned are the alkali metal salts, alkaline earth metal salts or substituted or unsubstituted ammonium salts of higher fatty acids ($C_{10}$–$C_{22}$), such as the Na salts or K salts of oleic or stearic acid, or of natural mixtures of fatty acids which can be obtained, for example, from coconut or tallow oil. Mention must also be made of the fatty acid methyltaurinates.

However, so-called synthetic surfactants are used more frequently, in particular fatty sulfonates, fatty sulfates, sulfonated benzimidazole derivatives or alkylarylsulfonates.

The fatty sulfonates or fatty sulfates are generally in the form of alkali metal salts, alkaline earth metal salts or substituted or unsubstituted ammonium salts, and have an alkyl radical having 8 to 22 C atoms, alkyl also including the alkyl moiety of acyl radicals, for example the Na or Ca salt of ligninsulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2-sulfonyl groups and one fatty acid radical having 8 to 22 C atoms. Examples of alkylarylsulfonates are the Na, Ca or triethanolamine salts of dodecylbenzenesulfonic acid, of dibutylnaphthalenesulfonic acid or of a naphthalenesulfonic acid/formaldehyde condensation product.

Other suitable compounds are the corresponding phosphates, such as the salts of the phosphoric ester of a p-nonylphenol/(4-14)-ethylene oxide adduct, or phospholipids.

Suitable non-ionic surfactants are mainly polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols.

Other non-ionic surfactants which are suitable are the water-soluble polyethylene oxide adducts with polypropylene glycol, ethylenediaminopolypropylene glycol and alkylpolypropylene glycol which have 1 to 10 carbon atoms in the alkyl chain and which contain 20 to 250 ethylene glycol ether groups and 10 to 100 propylene glycol ether groups, and the abovementioned compounds customarily contain 1 to 5 ethylene glycol units per propylene glycol unit.

Examples of non-ionic surfactants which may be mentioned are nonylphenolpolyethoxyethanols, castor oil polyethyleneglycol ethers, polypropylene/polyethylene oxide adducts, tributylphenoxypolyethoxyethanol, polyethylene glycol and octylphenoxypolyethoxyethanol. Other suitable substances are fatty acid esters of polyoxyethylenesorbitan, such as polyoxyethylenesorbitan trioleate.

The cationic surfactants are mainly quaternary ammonium salts, which contain at least one alkyl radical having 8 to 22 C atoms as N-substituents and which have lower halogenated or free alkyl, benzyl or lower hydroxyalkyl radicals as further substituents. The salts are preferably in the form of halides, methylsulfates or ethylsulfates, for example stearyltrimethylammonium chloride or benzyldi(2-chloroethyl)ethylammonium bromide.

The surfactants customary in the art of formulation are described, inter alia, in the following publications:

"McCutcheon's Detergents and Emulsifiers Annual" MC Publishing Corp., Ridgewood, N.J., 1981;

H. Stache, "Tensid-Taschenbuch [Surfactant Guide]", 2nd edition, C. Hanser Verlag, Munich, Vienna, 1981;

M. and J. Ash. "Encyclopedia of Surfactants", Vol. I–III, Chemical Publishing Co., New York, 1980–1981.

As a rule, the agrochemical preparations contain 0.1 to 95 %, in particular 0.1 to 80 %, of the active substance of the formula I, 1 to 99.9 % of a solid or liquid additive and 0 to 25% in particular 0.1 to 25 %, of a surfactant.

In particular, preferred formulations have the following composition: (%=percent by weight).

| Emulsifiable concentrates: | |
|---|---|
| Active ingredient: | 1 to 20%, 5 to 10% being preferred |
| Surface-active composition: | 5 to 30%, preferably 10 to 20% |
| Liquid carrier: | 50 to 94%, preferably 70 to 85% |
| Dusts: | |
| Active ingredient: | 0.1 to 10%, preferably 0.1 to 1% |
| Solid carrier: | 99.9 to 90%, preferably 99.9 to 99% |
| Suspension concentrates: | |
| Active ingredient: | 5 to 75%, preferably 10 to 50% |
| Water: | 94 to 24%, preferably 88 to 30% |
| Surface-active composition: | 1 to 40%, preferably 2 to 30% |
| Wettable powder: | |
| Active ingredient: | 0.5 to 90%, preferably 1 to 80% |
| Surface-active composition: | 0.5 to 20%, preferably 1 to 15% |
| Solid carrier material: | 5 to 99%, preferably 15 to 90%. |
| Granules: | |
| Active ingredient: | 0.5 to 30%, preferably 3 to 15% |
| Solid carrier material: | 99.5 to 70%, preferably 97 to 85%. |

While concentrated compositions are more preferred as commercial goods, the end user usually uses dilute compositons. The use forms can be diluted down to 0.001% of active substance. The application rates are usually 0.001 to 5 kg of active ingredient/ha, preferably 0.005 to 3 kg of active ingredient/ha.

The compositions can also contain further additions, such as stabilizers, defoamers, viscosity regulators, binders, tackifiers or also fertilizers or other active substances for achieving specific effects.

FORMULATION EXAMPLES

Example F1: Formulation examples of active substances of the formula I(%=percent by weight)

| a) Wettable powder | a) | b) | c) |
|---|---|---|---|
| Active substance No. 1.001 | 20% | 50% | 0.5 |
| Na ligninsulfonate | 5% | 5% | 5% |
| Na lauryl sulfate | 3% | — | — |
| Na diisobutylnaphthalenesulfonate | — | 6% | 6% |
| Octylphenol polyethylene glycol ether (7–8 mol of EO) | — | 2% | 2% |
| Highly-disperse silica | 5% | 27% | 27% |
| Kaolin | 67% | 10% | — |
| Sodium chloride | — | — | 59.5% |

The active substance is intimately mixed with the additives and thoroughly ground in a suitable mill. This gives wettable powders which can be diluted with water to give suspension of any desired concentration.

| b) Emulsion concentrate | a) | b) |
|---|---|---|
| Active substance No. 1.001 | 10% | 1% |
| Octylphenol polyethylene glycol ether (4–5 mol of EO) | 3% | 3% |
| Ca dodecylbenzenesulfonate | 3% | 3% |
| Castor oil polyglycol ether (36 mol of EO) | 4% | 4% |
| Cyclohexanone | 30% | 10% |
| Xylene mixture | 50% | 79% |

Emulsions of any desired concentration can be prepared from this concentrate by diluting it with water.

| C) Dusts | a) | b) |
|---|---|---|
| Active substance No. 1.002 | 0.1% | 1% |
| Talc | 99.9% | — |
| Kaolin | — | 99% |

Ready-to-use dusts are obtained by mixing the active substance with the carrier and grinding the mixture on a suitable mill.

| d) Extruder granules | a) | b) |
|---|---|---|
| Active substance No. 1.001 | 10% | 1% |
| Na ligninsulfonate | 2% | 2% |
| Carboxymethylcellulose | 1% | 1% |
| Kaolin | 87% | 96% |

The active substance is mixed with the additives, and the mixture is ground and moistened with water. This mixture is extruded and subsequently dried in a stream of air.

| e) Coated granules | |
|---|---|
| Active substance No. 1.001 | 3% |
| Polyethylene glycol (MW 200) | 3% |
| Kaolin | 94% |

The kaolin is moistened with polyethylene glycol and the finely-ground active substance is applied uniformly thereto in a mixer. Dust-free coated granules are obtained in this manner.

| f) Suspension concentrate | a) | b) |
|---|---|---|
| Active substance No. 1.002 | 40% | 5% |
| Ethylene glycol | 10% | 10% |
| Nonylphenol polyethylene glycol ether (15 mol of EO) | 6% | 1% |
| Na ligninsulfonate | 10% | 5% |
| Carboxymethylcellulose | 1% | 1% |
| 37% aqueous formaldehyde solution | 0.2% | 0.2% |
| Silicone oil in the form of 75% aqueous emulsion | 0.8% | 0.8% |
| Water | 32% | 77% |

The finely-ground active substance is mixed intimately with the additives. This gives a suspension concentrate, from which suspensions of any desired concentration can be prepared by diluting it with water.

| g) Salt solution | |
|---|---|
| Active substance No. 1.002 | 5% |
| Isopropylamine | 1% |
| Octylphenol polyethylene glycol ether | 3% |

| g) Salt solution | |
|---|---|
| (78 mol of EO) | |

PREPARATION EXAMPLES

Example H 1: Preparation of 2-isopropylthio-3-fluoropyridine (intermediate)

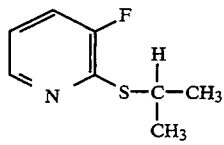

181.2 g of isopropylmercaptan are added dropwise at a temperature of 0° to +2° C. in the course of 25 minutes to a suspension of 324 g of anhydrous potassium carbonate and 335.6 g of 2,3-difluoropyridine in 4500 ml of dimethylformamide. After the reaction mixture has been stirred for 18 hours at room temperature, it is poured into a mixture of 8000 ml of ice-water and 4000 ml of ethyl acetate. The organic phase is subsequently separated off and washed with ice-water and then with ethyl acetate. The combined organic phases are dried with sodium sulfate and subsequently concentrated. Purification by column chromatography over silica gel with ethyl acetate/n-hexane (1:9) gives 362.9 g of 2-isopropylthio-3-fluoropyridine in the form of an oil.

Example H2: Preparation of 3-fluoropyridin-2-ylsulfonamide.(Compound No. 3.001)

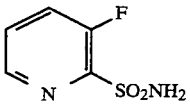

Varient a)

36.9 of gaseous chlorine is passed at a temperature of −5° C. in the course of 36 minutes into a mixture of 21.4 g of 2-isopropylthio-3-fluoropyridine, 340 ml of dichloromethane and 500 ml of 1 N hydrochloric acid. The mixture is subsequently stirred for 30 minutes at a temperature of 0° C., and nitrogen is intensively passed through the solution during the last 10 minutes. The organic phase is separated off, washed with ice-water and then with dichloromethane and dried over sodium sulfate.

The combined organic phases are subsequently added dropwise at a temperature of −75° C. to −50° C. in the course of 25 minutes to a mixture of 31.8 g of ammonia, dissolved in 63.6 ml of dichloromethane. After the cooling has been removed, the reaction mixture is stirred for 150 minutes and subsequently filtered. Concentration and chromatographic purification over silica gel with ethyl acetate/n-hexane (1:1) give 11.1 g of 3-fluoropyridin-2-ylsulfonamide (Compound No. 3.001 ) of a melting point of +124° to 125° C.

Variant b)

5.3 g (0.030 mol) of 3-aminopyridin-2-ylsulfonamide are dissolved in 12 ml of dimethyl sulfoxide, and the solution is added dropwise at 0° C. to 14.3 g (0.72 mol) of hydrogen fluoride (exothermal reaction). 2.4 g (0.035 mol) of sodium nitrite are then added in portions at 0° C. After one hour, the mixture is heated to 70° C. (evolution of N₂). After the reaction mixture has cooled, it is added to an ice/water mixture, sodium bicarbonate and sodium chloride are added, and the mixture is then extracted with tetrahydrofuran and ethyl acetate. The combined extracts are washed with a saturated sodium chloride solution, dried with magnesium sulfate, filtered and evaporated. The residue is stirred in diethyl ether/petroleum ether. Filtration gives 3.7 g of 3-fluoropyridin-2-ylsulfonamide (Compound No. 3.001) of a melting point of +124° to +125° C.

Example H3: Preparation of 3-mercaptopyridin-2-ylsulfonamide (Compound No. 3.008)

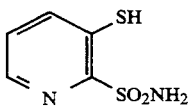

1.06 g of hydrogen sulfide are passed at a temperature of +16° to +20° C. under a nitrogen atmosphere into a mixture of 6.88 g of potassium tert-butylate and 5 g of 3-fluoropyridin-2-ylsulfonamide in 90 ml of dimethylformamide. After the mixture has been stirred for 4½ hours at a temperature of +50° C., 0.32 g of potassium tert-butylate are added and 0.1 g of hydrogen sulfide is passed in. After the reaction mixture has been stirred for 2 hours at a temperature of +50° C., it is concentrated in vacuo at a temperature of +75° C. The resulting oily residue is triturated with 135 ml of cold 0.75N sulfuric acid. After the residue has been filtered and washed with a little water, the resulting product is dried in vacuo over phosphorus pentoxide. This gives 3.58 g of 3-mercaptopyridin-2-ylsulfonamide of a melting point of +102 to +104° C.

Example H4: Preparation of 3-(3-fluoropropylthio)pyridin-2-ylsulfonamide (intermediate of the formula XX)

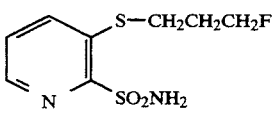

(XX)

A mixture consisting of 0.285 g of 3-mercaptopyridin-2-ylsulfonamide, 0.455 g of potassium carbonate, 5 ml of dry dimethylformamide and 0.23 g of 3-fluoro-1-bromopropane is stirred for 90 minutes at a temperature of +25° C. in a nitrogen atmosphere. The reaction mixture is subsequently added to an ice/water mixture. After a pH of 2 has been established with 2.8 ml of 2N HCl, the reaction mixture is extracted twice with ethyl acetate. The combined organic phases are washed three times with water and subsequently dried over sodium sulfate. Concentration and subsequent chromatographic purification of the residue over silica gel with ethyl acetate/n-hexane (1:1 ) give 0.12 g of 3-(3-fluoropropythio)-pyridin-2-ylsulfonamide of a melting point of 85° to +86° C.

Example H5: Preparation of 3-allylthiopyridin-2-ylsulfonamide

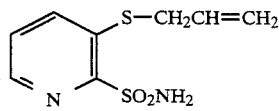

33.2 g (0.24 tool) of potassium carbonate as well as 1.32 g (0.005 tool) of 18-crown-6 and 15.8 g (0.17 tool) of 80 % allylmercaptan in 50 ml of acetonitrile are added to a solution, cooled to +5° C., of 17.62 g (0.1 mol) of 3-fluoropyridin-2-ylsulfonamide in 400 ml of acetonitrile.

After the reaction mixture has been stirred for 46 hours at room temperature, the precipitate which has formed is filtered off. The resulting filtrate is concentrated and purified by chromatography over a silica gel column using ethyl acetate/cyclohexane (2:1 ). This gives 10 g (50 % of theory) of 3-allylthiopyridin-2-ylsulfonamide.

Example H6: Preparation of 3-allylsulfonylpyridin-2-ylsulfonamide (Compound No. 2.001)

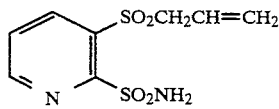

62.5 g of 40 % peracetic acid are added dropwise to a solution, cooled to +8° C., of 10 g (0.050 mol) of a 3-allylthiopyridin-2-ylsulfonamide, obtained as in Example H5, in 130 ml of acetic acid. The reaction mixture is subsequently stirred for 19 hours at a temperature of +8° to +30° C. The reaction mixture is subsequently poured into ice-water and extracted four times using ethyl acetate. The combined organic phases are washed with sodium hydrogen carbonate solution, treated with potassium sulfite and subsequently dried with magnesium sulfate. After the mixture has been filtered and the filtrate has been concentrated, the resulting residue is recrystallized from ethyl acetate/n-hexane and subsequently filtered.

Drying of the filter residue in vacuo at room temperature gives 8.1 g (62 % of theory) of 3-allylsulfonylpyridin-2-ylsulfonamide (Compound No. 2.001 ) of a melting point of +178° C.

Example H7: Preparation of N-(3-allylsulfonylpyridin-2-ylsulfonyl)-N'-(4,6-dimethoxypyrimidin-2-yl)urea (Compound No. 1.001)

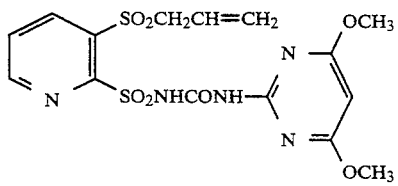

A solution of 4.66 g (0.029 mol) of 1,5-diazabicyclo[5.4.0]undec-5-ene in 15 ml of acetonitrile is added dropwise in the course of 10 minutes to a solution, cooled to +5° C., of 7.1 g (0.027 mol) of a 3-allylsulfonylpyridin-2-ylsulfonamide, obtained as in Example H6, in 90 ml of acetonitrile. After 7.8 g of N-(4,6-dimethoxypyrimidin-2-yl)phenylcarbamate have been added, the reaction mixture is stirred for 2 1/2 hours. After the acetonitrile has been distilled off under reduced pressure at a temperature of +45° C., a small amount of ice is added to the resulting residue and 15 ml of 2N hydrochloric acid are subsequently added.

After a small amount of diethyl ether has been added with vigorous stirring, the product starts to crystallize. The crystals are filtered off, washed with water and diethyl ether and again stirred with diethyl ether.

The residue is filtered and dried, and recrystallization from ethyl acetate/acetonitrile finally gives 8.1 g (68 % of theory) of N-(3-allylsulfonylpyridin-2-ylsulfonyl)-N'-(4,6-dimethoxypyrimidin-2-yl)urea (Compound No. 1.001) of a melting point of +185° C.

The compounds of the formula I listed in the following tables as well as the intermediates of the formulae II and III are prepared in an analogous manner.

TABLE 1

| No. | A | $R_1$ | $R_2$ | E | X | Y | Melting point [°C.] |
|---|---|---|---|---|---|---|---|
| 1.001 | —CH$_2$CH=CH$_2$ | H | H | CH | OCH$_3$ | OCH$_3$ | +185 (decomp.) |
| 1.002 | —CH$_2$CH$_2$OCH$_3$ | H | H | CH | OCH$_3$ | OCH$_3$ | +158 to +159 |
| 1.003 | —CH$_2$CH=CH$_2$ | H | H | CH | OCH$_3$ | CH$_3$ | +172 (decomp.) |
| 1.004 | —CH$_2$CH=CH$_2$ | H | H | CH | OCH$_3$ | Cl | |
| 1.005 | —CH$_2$CH=CH$_2$ | H | H | CH | OCHF$_2$ | OCHF$_2$ | |
| 1.006 | —CH$_2$CH=CH$_2$ | H | H | CH | OCHF$_2$ | OCH$_3$ | |
| 1.007 | —CH$_2$CH=CH$_2$ | H | H | CH | OCHF$_2$ | CH$_3$ | |
| 1.008 | —CH$_2$CH=CH$_2$ | H | H | N | OCH$_3$ | OCH$_3$ | +181 (decomp.) |
| 1.009 | —CH$_2$CH=CH$_2$ | H | H | N | OCH$_3$ | CH$_3$ | +170 (decomp.) |
| 1.010 | —CH$_2$CH=CH$_2$ | H | H | N | OC$_2$H$_5$ | CH$_3$ | |
| 1.011 | —CH$_2$CH=CH$_2$ | H | H | N | | NHCH$_3$ | |
| 1.012 | —CH$_2$CH=CH$_2$ | H | H | N | OCH$_3$ | N(CH$_3$)$_2$ | |
| 1.013 | —CH$_2$CH=CH$_2$ | H | H | N | OCH$_3$ | C$_3$H$_5$-cycl. | |
| 1.014 | —CH$_2$CH=CH$_2$ | H | H | N | OC$_2$H$_5$ | C$_3$H$_5$-cycl. | |
| 1.015 | —CH$_2$CH=CH$_2$ | 6-CH$_3$ | H | CH | OCH$_3$ | OCH$_3$ | |
| 1.016 | —CH$_2$CH=CH$_2$ | 6-CH$_3$ | H | N | OCH$_3$ | OCH$_3$ | |
| 1.017 | —CH$_2$CH=CH$_2$ | 6-CH$_3$ | H | N | OCH$_3$ | CH$_3$ | |
| 1.018 | —CH$_2$CH=CH$_2$ | 5-CH$_3$ | H | CH | OCH$_3$ | OCH$_3$ | |
| 1.019 | —CH$_2$CH=CH$_2$ | 5-CH$_3$ | H | N | OCH$_3$ | OCH$_3$ | |
| 1.020 | —CH$_2$CH=CH$_2$ | 5-CH$_3$ | H | N | OCH$_3$ | CH$_3$ | |
| 1.021 | —CH$_2$CH=CH$_2$ | 4-CH$_3$ | H | CH | OCH$_3$ | OCH$_3$ | |
| 1.022 | —CH$_2$CH=CH$_2$ | 4-CH$_3$ | H | N | OCH$_3$ | OCH$_3$ | |
| 1.023 | —CH$_2$CH=CH$_2$ | 4-CH$_3$ | H | N | OCH$_3$ | CH$_3$ | |
| 1.024 | —CH$_2$—C(CH$_3$)=CH$_2$ | H | H | CH | OCH$_3$ | OCH$_3$ | +166 (decomp.) |
| 1.025 | —CH$_2$—C(CH$_3$)=CH$_2$ | H | H | CH | OCH$_3$ | CH$_3$ | |
| 1.026 | —CH$_2$—C(CH$_3$)=CH$_2$ | H | H | CH | OCH$_3$ | Cl | |
| 1.027 | —CH$_2$—C(CH$_3$)=CH$_2$ | H | H | CH | OCH$_3$ | OCHF$_2$ | |
| 1.028 | —CH$_2$—C(CH$_3$)=CH$_2$ | H | H | CH | OCHF$_2$ | OCHF$_2$ | |
| 1.029 | —CH$_2$—C(CH$_3$)=CH$_2$ | H | H | N | OCH$_3$ | OCH$_3$ | |
| 1.030 | —CH$_2$—C(CH$_3$)=CH$_2$ | H | H | N | OCH$_3$ | CH$_3$ | |
| 1.031 | —CH$_2$—C(CH$_3$)=CH$_2$ | H | H | N | OC$_2$H$_5$ | CH$_3$ | |
| 1.032 | —CH$_2$—C(CH$_3$)=CH$_2$ | H | H | N | OC$_2$H$_5$ | NHCH$_3$ | |

TABLE 1-continued

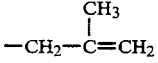

| No. | A | $R_1$ | $R_2$ | E | X | Y | Melting point [°C.] |
|---|---|---|---|---|---|---|---|
| 1.033 | −CH$_2$−C(CH$_3$)=CH$_2$ | H | H | N | OCH$_3$ | OCH$_3$ | |
| 1.034 | −CH$_2$−C(CH$_3$)=CH$_2$ | H | H | N | OC$_2$H$_5$ | C$_3$H$_5$-cycl. | |
| 1.035 | −CH$_2$−C(CH$_3$)=CH$_2$ | H | H | CH | OCHF$_2$ | CH$_3$ | |
| 1.036 | −CH$_2$−C(CH$_3$)=CH$_2$ | 6-CH$_3$ | H | CH | OCH$_3$ | OCH$_3$ | |
| 1.037 | −CH$_2$−C(CH$_3$)=CH$_2$ | 5-Cl | H | CH | OCH$_3$ | OCH$_3$ | |
| 1.038 | −CH$_2$−CH=CHCl | H | H | CH | OCH$_3$ | OCH$_3$ | |
| 1.039 | −CH$_2$−CH=CHCl | H | H | CH | OCH$_3$ | Cl | |
| 1.040 | −CH$_2$−CH=CHCl | H | H | CH | OCH$_3$ | CH$_3$ | |
| 1.041 | −CH$_2$−CH=CHCl | H | H | N | OCH$_3$ | CH$_3$ | |
| 1.042 | −CH$_2$−C(Cl)=CH$_2$ | H | H | CH | OCH$_3$ | OCH$_3$ | |
| 1.043 | −CH$_2$−C(Cl)=CH$_2$ | H | H | CH | OCH$_3$ | OCH$_3$ | |
| 1.044 | −CH$_2$−C(Cl)=CH$_2$ | H | H | CH | OCH$_3$ | Cl | |
| 1.045 | −CH$_2$−C(Cl)=CH$_2$ | H | H | N | OCH$_3$ | CH$_3$ | |
| 1.046 | −CH$_2$CH$_2$CH$_2$F | H | H | CH | OCH$_3$ | OCH$_3$ | +156 to +157 |
| 1.047 | −CH$_2$CH$_2$CH$_2$F | H | H | CH | OCH$_3$ | Cl | |
| 1.048 | −CH$_2$CH$_2$CH$_2$F | H | H | CH | OCH$_3$ | CH$_3$ | |
| 1.049 | −CH$_2$CH$_2$CH$_2$F | H | H | CH | OCH$_3$ | OCHF$_2$ | |
| 1.050 | −CH$_2$CH$_2$CH$_2$F | H | H | CH | OCH$_3$ | OCHF$_2$ | |
| 1.051 | −CH$_2$CH$_2$CH$_2$F | H | H | N | OCH$_3$ | CH$_3$ | |
| 1.052 | −CH$_2$CH$_2$CH$_2$F | H | H | N | OCH$_3$ | OCH$_3$ | |
| 1.053 | −CH$_2$CH$_2$CH$_2$F | H | H | N | OC$_2$H$_5$ | C$_3$H$_5$-cycl. | |
| 1.054 | −CH$_2$CH$_2$CH$_2$F | H | H | N | OC$_2$H$_5$ | CH$_3$ | |
| 1.055 | −CH$_2$CH$_2$CH$_2$F | H | H | N | OC$_2$H$_5$ | NHCH$_3$ | |
| 1.056 | −CH$_2$CH$_2$CH$_2$F | H | H | N | OCH$_3$ | N(CH$_3$)$_2$ | |
| 1.057 | −CH$_2$CH$_2$CH$_2$F | 6-CH$_3$ | H | CH | OCH$_3$ | OCH$_3$ | |
| 1.058 | −CH$_2$CH$_2$CH$_2$F | 6-CH$_3$ | H | CH | OCH$_3$ | Cl | |
| 1.059 | −CH$_2$CH$_2$CH$_2$F | 6-CH$_3$ | H | N | OCH$_3$ | OCH$_3$ | |
| 1.060 | −CH$_2$CH$_2$CH$_2$F | O−OCH$_3$ | H | CH | OCH$_3$ | OCH$_3$ | |
| 1.061 | −CH$_2$CH$_2$CH$_2$F | 6-F | H | CH | OCH$_3$ | OCH$_3$ | |
| 1.062 | −CH$_2$CH$_2$OCH$_3$ | H | H | CH | OCH$_3$ | CH$_3$ | |
| 1.063 | −CH$_2$CH$_2$OCH$_3$ | H | H | N | OCH$_3$ | CH$_3$ | |
| 1.064 | −CH$_2$CH=CH$_2$ | 5-Cl | H | CH | OCH$_3$ | OCH$_3$ | +153 to +156 (decomp.) |
| 1.065 | −CH$_2$CH=CH$_2$ | 5-Cl | H | CH | OCH$_3$ | CH$_3$ | |
| 1.066 | −CH$_2$CH=CH$_2$ | 5-Cl | H | N | OCH$_3$ | CH$_3$ | |
| 1.067 | −CH$_2$CH=CH$_2$ | 5-Cl | H | CH | OCH$_3$ | Cl | |
| 1.068 | −CH$_2$CH=CH$_2$ | 5-Cl | H | CH | CH$_3$ | CH$_3$ | |
| 1.069 | −CH(CH$_3$)CH$_2$F | H | H | CH | OCH$_3$ | OCH$_3$ | |
| 1.070 | −CH(CH$_3$)CH$_2$F | H | H | CH | Cl | OCH$_3$ | |
| 1.071 | −CH(CH$_3$)CH$_2$F | H | H | CH | OCH$_3$ | CH$_3$ | |
| 1.072 | −CH(CH$_3$)CH$_2$F | H | H | N | OCH$_3$ | CH$_3$ | |
| 1.073 | −CH(CH$_3$)CH$_2$F | H | H | N | OCH$_3$ | OCH$_3$ | |
| 1.074 | −CH(CH$_3$)CH$_2$F | H | H | N | OC$_2$H$_5$ | C$_3$H$_5$-cycl. | |
| 1.075 | −CH(CH$_3$)CH$_2$F | H | H | N | OC$_2$H$_5$ | CH$_3$ | |

TABLE 1-continued

[Structure: pyridine with R1, SO2-A, SO2NH-C(=O)-N(R2)-C(=N-)N= triazine/pyrimidine with X, Y, E]

| No. | A | R₁ | R₂ | E | X | Y | Melting point [°C.] |
|-----|---|-----|-----|---|---|---|---------------------|
| 1.076 | —CH(CH₃)CH₂F | 6-CH₃ | H | CH | OCH₃ | OCH₃ | |
| 1.077 | —CH(CH₃)CH₂F | 6-CH₃ | H | N | OCH₃ | CH₃ | |
| 1.078 | —CH(CH₂F)C₂H₅ | H | H | CH | OCH₃ | OCH₃ | |
| 1.079 | —CH(CH₂F)C₂H₅ | H | H | CH | Cl | OCH₃ | |
| 1.080 | —CH(CH₂F)C₂H₅ | H | H | N | OCH₃ | CH₃ | |
| 1.081 | —CH(CH₂F)CH₂F | H | H | N | OCH₃ | CH₃ | |
| 1.082 | —CH(CH₂F)CH₂F | H | H | CH | OCH₃ | OCH₃ | |
| 1.083 | —CH(CH₂F)CH₂F | H | H | CH | Cl | OCH₃ | |
| 1.084 | —CH(CH₂F)CH₂F | 6-CH₃ | H | CH | OCH₃ | OCH₃ | |
| 1.085 | —CH(CH₂F)CH₂F | 6-CH₃ | H | N | OCH₃ | CH₃ | |
| 1.086 | —CH(CH₂F)CH₂F | 6-CH₃ | H | N | OCH₃ | CH₃ | |
| 1.087 | —CH(CH₂F)C₂H₅ | 6-CH₃ | H | CH | OCH₃ | OCH₃ | |
| 1.088 | cyclopropyl-F | H | H | CH | OCH₃ | OCH₃ | |
| 1.089 | cyclopropyl-F,F | H | H | CH | OCH₃ | OCH₃ | |
| 1.090 | cyclopropyl-Cl | H | H | CH | OCH₃ | OCH₃ | |
| 1.091 | cyclobutyl-Cl | H | H | N | OCH₃ | CH₃ | |
| 1.092 | cyclopentyl-F | H | H | CH | OCH₃ | CH₃ | |
| 1.093 | cyclopentyl-Cl | H | H | CH | OCH₃ | CH₃ | |
| 1.094 | cyclohexyl-Br | H | H | CH | OCH₃ | OCH₃ | |
| 1.095 | cyclohexyl-Cl,Cl | H | H | CH | OCH₃ | OCH₃ | |
| 1.096 | —CH₂-cyclopentenyl | H | H | CH | OCH₃ | OCH₃ | |

TABLE 1-continued

| No. | A | $R_1$ | $R_2$ | E | X | Y | Melting point [°C.] |
|---|---|---|---|---|---|---|---|
| 1.097 | —CH$_2$—CH$_2$—(cyclohexenyl) | H | H | CH | OCH$_3$ | OCH$_3$ | |
| 1.098 | (2-methoxycyclohexyl) | H | H | CH | OCH$_3$ | OCH$_3$ | |
| 1.099 | (3-methylthiocyclopentyl) | H | H | CH | OCH$_3$ | OCH$_3$ | |
| 1.100 | —CH$_2$CH$_2$.CH$_2$—(cyclopentenyl) | H | H | CH | OCH$_3$ | OCH$_3$ | |
| 1.101 | —CH$_2$—CH$_2$—CH$_2$—(cyclohexenyl) | H | H | CH | CH$_3$ | CH$_3$ | |
| 1.102 | —CH$_2$CH=CH$_2$ | 6-OCH$_3$ | H | CH | OCH$_3$ | OCH$_3$ | |
| 1.103 | —CH$_2$CH=CH$_2$ | H | CH$_3$ | CH | OCH$_3$ | OCH$_3$ | |
| 1.104 | —CH$_2$CH=CH$_2$ | 5-OCH$_3$ | H | CH | OCH$_3$ | OCH$_3$ | |
| 1.105 | —CH$_2$CH=CH$_2$ | 6-OCH$_3$ | H | CH | CH$_3$ | OCH$_3$ | |
| 1.106 | —CH$_2$CH=CH$_2$ | 6-OCH$_3$ | H | CH | OCH$_3$ | OCH$_3$ | |
| 1.107 | —CH$_2$C≡CH | H | H | CH | OCH$_3$ | OCH$_3$ | |
| 1.108 | —CH$_2$C≡CH | H | H | N | OCH$_3$ | OCH$_3$ | |
| 1.109 | —CH$_2$C≡CH | H | H | CH | OCH$_3$ | CH$_3$ | |
| 1.110 | —CH$_2$C≡CH | 6-CH$_3$ | H | CH | OCH$_3$ | OCH$_3$ | |
| 1.111 | —CH$_2$C≡CH | 6-OCH$_3$ | H | CH | OCH$_3$ | OCH$_3$ | |
| 1.112 | —CH$_2$C≡CH | H | H | CH | OCH$_3$ | OCHF$_2$ | |
| 1.113 | —CH$_2$C≡CH | H | H | CH | OCHF$_2$ | OCHF$_2$ | |
| 1.114 | —CH$_2$CH$_2$CH=CH$_2$ | H | H | CH | OCH$_3$ | OCH$_3$ | +168 (decomp.) |
| 1.115 | —CH$_2$CH$_2$CH=CH$_2$ | H | H | CH | CH$_3$ | OCH$_3$ | |
| 1.116 | —CH$_2$CH$_2$CH=CH$_2$ | H | H | N | OCH$_3$ | OCH$_3$ | |
| 1.117 | —CH$_2$CH$_2$CH=CH$_2$ | H | H | CH | OCH$_3$ | OCHF$_2$ | |
| 1.118 | —CH$_2$CH$_2$CH=CH$_2$ | 6-CH$_3$ | H | CH | OCH$_3$ | OCH$_3$ | |
| 1.119 | —CH$_2$CH$_2$CH=CH$_2$ | 6-CH$_3$ | H | N | OCH$_3$ | OCH$_3$ | |
| 1.120 | —CH$_2$CH$_2$CH=CH$_2$ | 5-CH$_3$ | H | CH | OCH$_3$ | OCH$_3$ | |
| 1.121 | —CH$_2$CH$_2$CH=CH$_2$ | 5-CH$_3$ | H | CH | OCH$_3$ | OCHF$_2$ | |
| 1.122 | —CH$_2$CH$_2$CH=CH$_2$ | 4-CH$_3$ | H | CH | OCH$_3$ | OCH$_3$ | |
| 1.123 | —CH$_2$CH$_2$CH=CH$_2$ | 4-CH$_3$ | H | N | OCH$_3$ | OCH$_3$ | |
| 1.124 | —CH$_2$CH$_2$CH=CH$_2$ | 4-CH$_3$ | H | CH | OCH$_3$ | N(CH$_3$)$_2$ | |
| 1.125 | —CH$_2$CH$_2$CH=CH$_2$ | 6-OCH$_3$ | H | CH | OCH$_3$ | OCH$_3$ | |
| 1.126 | —CH$_2$CH$_2$CH=CH$_2$ | 6-OCH$_3$ | H | N | OCH$_3$ | OCH$_3$ | |
| 1.127 | —CH(CH$_3$)CH=CH$_2$ | H | H | CH | OCH$_3$ | OCH$_3$ | +113 (decomp.) |
| 1.128 | —CH(CH$_3$)CH=CH$_2$ | H | H | N | OCH$_3$ | OCH$_3$ | |
| 1.129 | —CH(CH$_3$)CH=CH$_2$ | H | H | CH | OCH$_3$ | CH$_3$ | |
| 1.130 | —CH(CH$_3$)CH=CH$_2$ | H | H | CH | OCH$_3$ | OCHF$_2$ | |
| 1.131 | —CH(CH$_3$)CH=CH$_2$ | 6-CH$_3$ | H | CH | OCH$_3$ | OCH$_3$ | |
| 1.132 | —CH(CH$_3$)CH=CH$_2$ | 6-CH$_3$ | H | N | OCH$_3$ | OCH$_3$ | |
| 1.133 | —CH(CH$_3$)CH=CH$_2$ | 6-OCH$_3$ | H | CH | OCH$_3$ | OCH$_3$ | |
| 1.134 | —CH(CH$_3$)CH=CH$_2$ | 6-OCH$_3$ | H | N | OCH$_3$ | OCH$_3$ | |
| 1.135 | —CH(CH$_3$)CH=CH$_2$ | 5-CH$_3$ | N | CH | OCH$_3$ | OCH$_3$ | |
| 1.136 | —CH(CH$_3$)CH=CH$_2$ | 5-Cl | H | CH | OCH$_3$ | OCH$_3$ | |
| 1.137 | —CH(CH$_3$)CH=CH$_2$ | 4-CH$_3$ | H | CH | OCH$_3$ | OCH$_3$ | |
| 1.138 | —CH(CH$_3$)CH=CH$_2$ | 4-CH$_3$ | H | CH | OCH$_3$ | N(CH$_3$)$_2$ | |

TABLE 1-continued

| No. | A | R₁ | R₂ | E | X | Y | Melting point [°C.] |
|---|---|---|---|---|---|---|---|
| 1.139 | —CH(CH₃)CH=CH₂ | 4-CH₃ | H | N | OCH₃ | OCH₃ | |
| 1.140 | —CH₂CH=CHCH₃ | H | H | CH | OCH₃ | OCH₃ | |
| 1.141 | —CH₂CH=CHCH₃ | H | H | N | OCH₃ | OCH₃ | |
| 1.142 | —CH₂CH=CHCH₃ | H | H | CH | OCH₃ | CH₃ | |
| 1.143 | —CH₂CH=CHCH₃ | H | H | CH | OCH₃ | OCHF₂ | |
| 1.144 | —CH₂CH=CHCH₃ | 6-CH₃ | H | CH | OCH₃ | OCH₃ | |
| 1.145 | —CH₂CH=CHCH₃ | 6-CH₃ | H | N | OCH₃ | OCH₃ | |
| 1.146 | —CH₂CH=CHCH₃ | 6-OCH₃ | H | CH | OCH₃ | OCH₃ | |
| 1.147 | —CH₂CH=CHCH₃ | 6-OCH₃ | H | N | OCH₃ | OCH₃ | |
| 1.148 | —CH₂CH=CHCH₃ | 5-CH₃ | H | CH | OCH₃ | OCH₃ | |
| 1.149 | —CH₂CH=CHCH₃ | 4-CH₃ | H | CH | OCH₃ | OCH₃ | |
| 1.150 | —CH₂CH=CHCH₃ | 4-CH₃ | H | CH | OCH₃ | N(CH₃)₂ | |
| 1.151 | —CH₂—C≡C—CH₃ | H | H | CH | OCH₃ | OCH₃ | |
| 1.152 | —CH₂—C≡C—CH₃ | H | H | N | OCH₃ | OCH₃ | |
| 1.153 | —CH₂—C≡C—CH₃ | H | H | CH | CH₃ | CH₃ | |
| 1.154 | —CH₂—C≡C—CH₃ | H | H | CH | OCH₃ | OCHF₂ | |
| 1.155 | —CH₂—C≡C—CH₃ | 6-CH₃ | H | CH | OCH₃ | OCH₃ | |
| 1.156 | —CH₂—C≡C—CH₃ | 6-OCH₃ | H | CH | OCH₃ | OCH₃ | |
| 1.157 | —CH₂—C≡C—CH₃ | 6-OCHF₂ | H | CH | OCH₃ | OCH₃ | |
| 1.158 | —CH₂—C≡C—CH₃ | 5-CH₃ | H | CH | OCH₃ | OCH₃ | |
| 1.159 | —CH₂—C≡C—CH₃ | 4-CH₃ | H | CH | OCH₃ | OCH₃ | |
| 1.160 | —CH₂—C≡C—CH₃ | 4-CH₃ | H | CH | OCH₃ | N(CH₃)₂ | |
| 1.161 | —CH₂CH₂C≡CH | H | H | CH | OCH₃ | OCH₃ | |
| 1.162 | —CH₂CH₂C≡CH | H | H | N | OCH₃ | OCH₃ | |
| 1.163 | —CH₂CH₂C≡CH | H | H | CH | OCH₃ | CH₃ | |
| 1.164 | —CH₂CH₂C≡CH | H | H | CH | OCH₃ | OCHF₂ | |
| 1.165 | —CH₂CH₂C≡CH | 6-CH₃ | H | CH | OCH₃ | OCH₃ | |
| 1.166 | —CH₂CH₂C≡CH | 6-OCH₃ | H | CH | OCH₃ | OCH₃ | |
| 1.167 | —CH₂CH₂C≡CH | 6-OCHF₂ | H | CH | OCH₃ | OCH₃ | |
| 1.168 | —CH₂CH₂C≡CH | 5-CH₃ | H | CH | OCH₃ | OCH₃ | |
| 1.169 | —CH₂CH₂C≡CH | 4-CH₃ | H | CH | OCH₃ | OCH₃ | |
| 1.170 | —CH₂CH₂C≡CH | 6-OCHF₂ | H | CH | OCH₃ | OCH₃ | |
| 1.171 | —CH₂CH=CHCl (E) | H | H | CH | OCH₃ | OCH₃ | +184 (decomp.) |
| 1.172 | —CH₂CH=CHCl (E) | H | H | N | OCH₃ | OCH₃ | |
| 1.173 | —CH₂CH=CHCl (E) | H | H | CH | OCH₃ | CH₃ | |
| 1.174 | —CH₂CH=CHCl (E) | H | H | CH | OCH₃ | OCHF₂ | |
| 1.175 | —CH₂CH=CHCl (E) | 6-CH₃ | H | CH | OCH₃ | OCH₃ | |
| 1.176 | —CH₂CH=CHCl (E) | 6-OCH₃ | H | CH | OCH₃ | OCH₃ | |
| 1.177 | —CH₂CH=CHCl (E) | 5-CH₃ | H | CH | OCH₃ | OCH₃ | |
| 1.178 | —CH₂CH=CHCl (E) | 4-CH₃ | H | CH | OCH₃ | OCH₃ | |
| 1.179 | —CH₂CH=CHCl (E) | 6-OCH₃ | H | N | OCH₃ | OCH₃ | |
| 1.180 | —CH₂CH=CHCl (Z) | H | H | CH | OCH₃ | OCH₃ | +151 to +152 (decomp.) |
| 1.181 | —CH₂CH=CHCl (Z) | H | N | CH | OCH₃ | OCH₃ | |
| 1.182 | —CH₂CH=CHCl (Z) | H | H | CH | OCH₃ | CH₃ | |
| 1.183 | —CH₂CH=CHCl (Z) | H | H | CH | OCH₃ | OCHF₂ | |
| 1.184 | —CH₂CH=CHCl (Z) | 6-CH₃ | H | CH | OCH₃ | OCH₃ | |
| 1.185 | —CH₂CH=CHCl (Z) | 6-OCH₃ | H | CH | OCH₃ | OCH₃ | |
| 1.186 | —CH₂CH=CHCl (Z) | 6-OCH₃ | H | N | OCH₃ | OCH₃ | |
| 1.187 | —CH₂CH=CHCl (Z) | 5-CH₃ | H | CH | OCH₃ | OCH₃ | |
| 1.188 | —CH₂CH=CHCl (Z) | 4-CH₃ | H | CH | OCH₃ | OCH₃ | |
| 1.189 | —CH₂CH=CHCl (Z) | 4-CH₃ | H | N | OCH₃ | OCH₃ | |
| 1.190 | —CH₂CH=CHCl (Z) | 4-CH₃ | H | CH | OCH₃ | N(CH₃)₂ | |
| 1.191 | —CH₂CH=CHCl (Z) | 6-OCHF₂ | H | CH | OCH₃ | OCH₃ | |
| 1.192 | —CH₂CH=CHCF₃ | H | H | CH | OCH₃ | OCH₃ | |
| 1.193 | —CH₂CH=CHCF₃ | H | H | N | OCH₃ | OCH₃ | |
| 1.194 | —CH₂CH=CHCF₃ | H | H | CH | OCH₃ | CH₃ | |
| 1.195 | —CH₂CH=CHBr (Z/E) | H | H | CH | OCH₃ | OCH₃ | +157 to 158 (decomp.) |
| 1.196 | —CH₂CH=CHBr (Z/E) | H | H | N | OCH₃ | OCH₃ | |
| 1.197 | —CH₂CH=CHBr (Z/E) | H | H | CH | OCH₃ | CH₃ | |
| 1.198 | —CH₂CH=CHBr (Z/E) | H | H | CH | OCH₃ | OCHF₂ | |
| 1.199 | —CH₂CH=CHBr (Z/E) | 6-CH₃ | H | CH | OCH₃ | OCH₃ | |
| 1.200 | —CH₂CH=CHBr (Z/E) | 6-CH₃ | H | N | OCH₃ | OCH₃ | |
| 1.201 | —CH₂CH=CHBr (Z/E) | 6-OCH₃ | H | CH | OCH₃ | OCH₃ | |
| 1.202 | —CH₂CH=CHBr (Z/E) | 6-OCH₃ | H | N | OCH₃ | OCH₃ | |
| 1.203 | —CH₂CH=CHBr (Z/E) | 5-CH₃ | H | CH | OCH₃ | OCH₃ | |
| 1.204 | —CH₂CH=CHBr (Z/E) | 4-CH₃ | H | CH | OCH₃ | OCH₃ | |
| 1.205 | —CH₂CH=CHBr (Z/E) | 4-CH₃ | H | N | OCH₃ | OCH₃ | |
| 1.206 | —CH₂CH=CHBr (Z/E) | 4-CH₃ | H | CH | OCH₃ | N(CH₃)₂ | |

TABLE 1-continued

| No. | A | R₁ | R₂ | E | X | Y | Melting point [°C.] |
|-----|---|----|----|---|---|---|---------------------|
| 1.207 | —CH₂—(cyclohexenyl) | H | H | CH | OCH₃ | OCH₃ | |
| 1.208 | —CH₂—(cyclohexenyl) | H | H | N | OCH₃ | OCH₃ | |
| 1.209 | —CH₂—(cyclohexenyl) | 6-CH₃ | H | CH | OCH₃ | OCH₃ | |
| 1.210 | —CH₂—(cyclohexenyl) | 6-CH₃ | H | N | OCH₃ | OCH₃ | |
| 1.211 | —CH₂—(cyclohexenyl) | 6-OCH₃ | H | CH | OCH₃ | OCH₃ | |
| 1.212 | —CH₂—(cyclohexenyl) | 6-OCH₃ | N | N | OCH₃ | OCH₃ | |
| 1.213 | —CH₂—(cyclohexenyl) | 5-CH₃ | H | CH | OCH₃ | OCH₃ | |
| 1.214 | —CH₂—(cyclohexenyl) | H | H | CH | OCH₃ | OCH₃ | |
| 1.215 | —CH₂—(cyclohexenyl) | H | H | N | OCH₃ | OCH₃ | |
| 1.216 | —CH₂—(cyclohexenyl) | H | H | CH | OCH₃ | OCH₃ | |
| 1.217 | —CH₂—(cyclohexenyl) | H | H | CH | OCH₃ | OCHF₂ | |
| 1.218 | —CH₂—(cyclohexenyl) | 6-CH₃ | H | CH | OCH₃ | OCH₃ | |

TABLE 1-continued

Structure: R₁-pyridine with SO₂-A, SO₂NH-C(O)-N(R₂)-C(=N-X-E-Y)...

| No. | A | R₁ | R₂ | E | X | Y | Melting point [°C.] |
|---|---|---|---|---|---|---|---|
| 1.219 | -CH₂-(cyclohexenyl) | 6-CH₃ | H | CH | OCH₃ | OCH₃ | |
| 1.220 | -CH₂-(cyclohexenyl) | 6-OCHF₂ | H | CH | OCH₃ | OCH₃ | |
| 1.221 | -CH₂-(cyclohexenyl) | 5-CH₃ | H | CH | OCH₃ | OCH₃ | |
| 1.222 | oxetanyl | H | H | CH | OCH₃ | OCH₃ | |
| 1.223 | oxetanyl | H | H | N | OCH₃ | OCH₃ | |
| 1.224 | oxetanyl | H | H | CH | OCH₃ | CH₃ | |
| 1.225 | oxetanyl | 6-CH₃ | H | CH | OCH₃ | OCH₃ | |
| 1.226 | oxetanyl | 6-OCH₃ | H | CH | OCH₃ | OCH₃ | |
| 1.227 | oxetanyl | H | H | CH | OCH₃ | OCHF₂ | |
| 1.228 | oxetanyl | 5-Cl | H | CH | OCH₃ | OCH₃ | |
| 1.229 | tetrahydrofuranyl | H | H | CH | OCH₃ | OCH₃ | |
| 1.230 | tetrahydrofuranyl | H | H | N | OCH₃ | OCH₃ | |

TABLE 1-continued

| No. | A | $R_1$ | $R_2$ | E | X | Y | Melting point [°C.] |
|---|---|---|---|---|---|---|---|
| 1.231 | tetrahydrofuran-2-yl | H | H | CH | $OCH_3$ | $CH_3$ | |
| 1.232 | tetrahydrofuran-2-yl | 6-$CH_3$ | H | CH | $OCH_3$ | $OCH_3$ | |
| 1.233 | tetrahydrofuran-2-yl | 6-$OCH_3$ | H | CH | $OCH_3$ | $OCH_3$ | |
| 1.234 | tetrahydrofuran-2-yl | H | H | CH | $OCH_3$ | $OCHF_2$ | |
| 1.235 | tetrahydrofuran-2-yl | 6-$OCHF_2$ | H | CH | $OCH_3$ | $OCH_3$ | |
| 1.236 | $-CH_2-$oxetan-3-yl | H | H | CH | $OCH_3$ | $OCH_3$ | |
| 1.237 | $-CH_2-$oxetan-3-yl | H | H | N | $OCH_3$ | $OCH_3$ | |
| 1.238 | $-CH_2-$oxetan-3-yl | H | H | CH | $OCH_3$ | $CH_3$ | |
| 1.239 | $-CH_2-$oxetan-3-yl | 6-$CH_3$ | H | CH | $OCH_3$ | $OCH_3$ | |
| 1.240 | $-CH_2-$oxetan-3-yl | 6-$OCH_3$ | H | CH | $OCH_3$ | $OCH_3$ | |
| 1.241 | $-CH_2-$oxetan-3-yl | H | H | CH | $OCH_3$ | $OCHF_2$ | |
| 1.242 | $-CH_2-$oxetan-3-yl | 6-$OCHF_2$ | H | CH | $OCH_3$ | $OCH_3$ | |
| 1.243 | $-CH_2-$tetrahydrofuran-2-yl | H | H | CH | $OCH_3$ | $OCH_3$ | +138 to +139 |

TABLE 1-continued

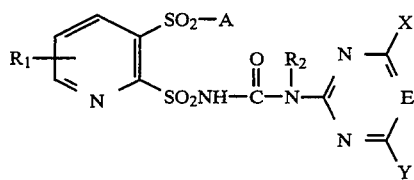

| No. | A | R₁ | R₂ | E | X | Y | Melting point [°C.] |
|---|---|---|---|---|---|---|---|
| 1.244 | −CH₂−(tetrahydrofuran-2-yl) | H | H | N | OCH₃ | OCH₃ | |
| 1.245 | −CH₂−(tetrahydrofuran-2-yl) | H | H | CH | OCH₃ | CH₃ | |
| 1.246 | −CH₂−(tetrahydrofuran-2-yl) | H | H | CH | OCH₃ | OCHF₂ | |
| 1.247 | −CH₂−(tetrahydrofuran-2-yl) | 6-CH₃ | H | CH | OCH₃ | OCH₃ | |
| 1.248 | −CH₂−(tetrahydrofuran-2-yl) | 6-OCH₃ | H | CH | OCH₃ | OCH₃ | |
| 1.249 | −CH₂−(tetrahydropyran-2-yl) | H | H | CH | OCH₃ | OCH₃ | |
| 1.250 | −CH₂−(tetrahydropyran-2-yl) | H | H | N | OCH₃ | OCH₃ | |
| 1.251 | −CH₂−(tetrahydropyran-2-yl) | H | H | CH | OCH₃ | CH₃ | |
| 1.252 | −CH₂−(tetrahydropyran-2-yl) | H | H | CH | OCH₃ | OCHF₂ | |
| 1.253 | −CH₂−(tetrahydropyran-2-yl) | 6-CH₃ | H | CH | OCH₃ | OCH₃ | |
| 1.254 | −CH₂−(tetrahydropyran-2-yl) | 6-OCH₃ | H | CH | OCH₃ | OCH₃ | |
| 1.255 | −CH₂−(tetrahydropyran-2-yl) | 6-OCHF₂ | H | CH | OCH₃ | OCH₃ | |

TABLE 1-continued

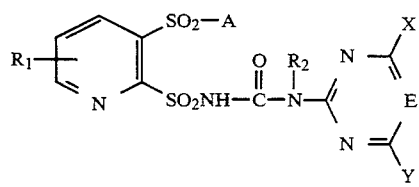

| No. | A | R₁ | R₂ | E | X | Y | Melting point [°C.] |
|---|---|---|---|---|---|---|---|
| 1.256 | cyclobutyl-SO₂ | H | H | CH | OCH₃ | OCH₃ | |
| 1.257 | cyclobutyl-SO₂ | H | H | N | OCH₃ | OCH₃ | |
| 1.258 | cyclobutyl-SO₂ | H | H | CH | OCH₃ | OCH₃ | |
| 1.259 | cyclobutyl-SO₂ | H | H | CH | OCH₃ | OCHF₂ | |
| 1.260 | cyclobutyl-SO₂ | 6-CH₃ | H | CH | OCH₃ | OCH₃ | |
| 1.261 | cyclobutyl-SO₂ | 6-OCH₃ | H | CH | OCH₃ | OCH₃ | |
| 1.262 | cyclobutyl-SO₂ | 5-CH₃ | H | CH | OCH₃ | OCH₃ | |
| 1.263 | cyclobutyl-SO₂ | 4-CH₃ | H | CH | OCH₃ | OCH₃ | |
| 1.264 | cyclobutyl-SO₂ | 6-OCHF₂ | H | CH | OCH₃ | OCH₃ | |
| 1.265 | N-methylpiperidinyl | H | H | CH | OCH₃ | OCH₃ | |
| 1.266 | N-methylpiperidinyl | H | H | N | OCH₃ | OCH₃ | |
| 1.267 | N-methylpiperidinyl | H | H | CH | OCH₃ | CH₃ | |

TABLE 1-continued

Structure: R₁-pyridine with SO₂-A at one position and SO₂NH-C(O)-N(R₂)-C(=N-)... linked to a ring containing N=X, N=Y, E

| No. | A | R₁ | R₂ | E | X | Y | Melting point [°C.] |
|---|---|---|---|---|---|---|---|
| 1.268 | 4-(N-methyl)piperidinyl | 6-CH₃ | H | CH | OCH₃ | OCH₃ | |
| 1.269 | 4-(N-methyl)piperidinyl | 6-OCH₃ | H | CH | OCH₃ | OCH₃ | |
| 1.270 | tetrahydrothiophene-SO₂ (sulfolanyl) | H | H | CH | OCH₃ | OCH₃ | |
| 1.271 | sulfolanyl | H | H | N | OCH₃ | OCH₃ | |
| 1.272 | sulfolanyl | H | H | CH | OCH₃ | CH₃ | |
| 1.273 | sulfolanyl | H | H | CH | OCH₃ | OCH₃ | |
| 1.274 | sulfolanyl | 6-CH₃ | H | CH | OCH₃ | OCH₃ | |
| 1.275 | sulfolanyl | 6-OCH₃ | H | CH | OCH₃ | OCH₃ | |
| 1.276 | sulfolanyl | 6-OCHF₂ | H | CH | OCH₃ | OCH₃ | |
| 1.277 | -CH₂-sulfolanyl | H | H | CH | OCH₃ | OCH₃ | |
| 1.278 | -CH₂-sulfolanyl | H | H | N | OCH₃ | OCH₃ | |
| 1.279 | -CH₂-sulfolanyl | H | H | CH | OCH₃ | CH₃ | |
| 1.280 | -CH₂-sulfolanyl | 6-CH₃ | H | CH | OCH₃ | OCH₃ | |

TABLE 1-continued

Structure: pyridine with R₁, SO₂-A, SO₂NH-C(=O)-N(R₂)-C(=N-X)(N=Y) with E

| No. | A | R₁ | R₂ | E | X | Y | Melting point [°C.] |
|---|---|---|---|---|---|---|---|
| 1.281 | —CH₂-(tetrahydrothiophene-SO₂) | 6-OCH₃ | H | CH | OCH₃ | OCH₃ | |
| 1.282 | —CHF₂ | H | H | CH | OCH₃ | OCH₃ | |
| 1.283 | —CHF₂ | H | H | CH | OCH₃ | CH₃ | |
| 1.284 | —CHF₂ | H | H | N | OCH₃ | CH₃ | |
| 1.285 | —CHF₂ | H | H | N | OCH₃ | OCH₃ | |
| 1.286 | —CF₂CHF₂ | H | H | N | OCH₃ | OCH₃ | |
| 1.287 | —CF₂CHF₂ | H | H | N | OCH₃ | CH₃ | |
| 1.288 | —CF₂CHF₂ | H | H | CH | OCH₃ | CH₃ | |
| 1.289 | —CF₂CHF₂ | H | H | CH | OCH₃ | OCH₃ | |
| 1.290 | —CF₂CHF₂ | H | H | CH | CH₃ | CH₃ | |
| 1.291 | —CH₂CH₂N(CH₃)₂ | H | H | CH | CH₃ | CH₃ | |
| 1.292 | —CH₂CH₂N(CH₃)₂ | H | H | CH | OCH₃ | OCH₃ | |
| 1.293 | —CH₂CH₂N(CH₃)₂ | H | H | N | OCH₃ | OCH₃ | |
| 1.294 | —CH₂CH₂N(CH₃)₂ | H | H | N | OCH₃ | CH₃ | |
| 1.295 | —CH₂CH₂N(C₂H₅)₂ | H | H | CH | OCH₃ | OCH₃ | |
| 1.296 | —CH₂CH₂N(C₂H₅)₂ | H | H | CH | OCH₃ | CH₃ | |
| 1.297 | —CH₂CH₂N(C₂H₅)₂ | H | H | CH | OCH₃ | OCH₃ | |
| 1.298 | —CH₂CH₂NHCH₃ | H | H | CH | OCH₃ | OCH₃ | |
| 1.299 | —CH₂CH₂NHCH₃ | H | H | CH | OCH₃ | CH₃ | |
| 1.300 | —CH₂CH₂NHCH₃ | H | H | N | OCH₃ | CH₃ | |
| 1.301 | —CH(CH₃)CH₂OCH₃ | H | H | N | CH₃ | OCH₃ | |
| 1.302 | —CH(CH₃)CH₂OCH₃ | H | H | CH | OCH₃ | OCH₃ | +136 to +138 |
| 1.303 | —CH(CH₃)CH₂OCH₃ | 6-CH₃ | H | CH | OCH₃ | OCH₃ | |
| 1.304 | —CH(CH₃)CH₂OCH₃ | 6-CH₃ | H | N | OCH₃ | CH₃ | |
| 1.305 | —CH(CH₃)CH₂OCH₃ | H | H | CH | CH₃ | CH₃ | |
| 1.306 | —CH(CH₃)CH₂OCH₃ | H | H | CH | OCH₃ | CH₃ | |
| 1.307 | —CH₂CH₂SO₂CH₃ | H | H | CH | OCH₃ | OCH₃ | +133 to +137 |
| 1.308 | —CH₂CH₂SO₂CH₃ | H | H | CH | OCH₃ | CH₃ | |
| 1.309 | —CH₂CH₂SO₂CH₃ | H | H | N | OCH₃ | CH₃ | |
| 1.310 | —CH₂CH₂SO₂CH₃ | H | H | N | OCH₃ | OCH₃ | |
| 1.311 | —CH₂CH₂CH₂Cl | H | H | N | OCH₃ | OCH₃ | +166 to +168 |
| 1.312 | —CH₂CH₂CH₂Cl | H | H | N | OCH₃ | OCH₃ | |
| 1.313 | —CH₂CH₂CH₂Cl | H | H | N | OCH₃ | CH₃ | |
| 1.314 | —CH₂CH₂CH₂Cl | 6-CH₃ | H | N | OCH₃ | CH₃ | |
| 1.315 | —CH₂CH₂CH₂Cl | 6-CH₃ | H | CH | OCH₃ | CH₃ | |
| 1.316 | —CH₂CH₂CH₂Cl | 6-CH₃ | H | CH | OCH₃ | OCH₃ | |
| 1.317 | —CH(CH₃)CH₂Cl | H | H | CH | OCH₃ | OCH₃ | +145 to +148 |
| 1.318 | —CH(CH₃)CH₂Cl | H | H | N | OCH₃ | OCH₃ | |
| 1.319 | —CH(CH₃)CH₂Cl | H | H | N | OCH₃ | CH₃ | |

TABLE 1-continued

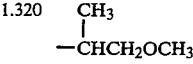

| No. | A | R₁ | R₂ | E | X | Y | Melting point [°C.] |
|---|---|---|---|---|---|---|---|
| 1.320 | —CH(CH₃)CH₂OCH₃ | H | H | CH | OCH₃ | Cl | |
| 1.321 | —CH₂CH₂CH₂Cl | H | H | CH | OCH₃ | Cl | |

TABLE 2

Structure (II): pyridine with R₁, SO₂—A, and SO₂NH₂ substituents.

| No. | A | R₁ | Melting point [°C.] |
|---|---|---|---|
| 2.001 | —CH₂CH=CH₂ | H | +178 |
| 2.002 | —CH₂CH₂OCH₃ | H | |
| 2.003 | —CH₂CH=CH₂ | 6-CH₃ | |
| 2.004 | —CH₂CH=CH₂ | 5-CH₃ | |
| 2.005 | —CH₂CH=CH₂ | 4-CH₃ | |
| 2.006 | —CH₂—C(CH₃)=CH₂ | H | +180 |
| 2.007 | —CH₂—C(CH₃)=CH₂ | 6-CH₃ | |
| 2.008 | —CH₂—C(CH₃)=CH₂ | 5-Cl | |
| 2.009 | —CH₂CH=CH₂ | 5-Cl | +193 to +195 (decomp.) |
| 2.010 | —CH₂CH=CHCl | H | |
| 2.011 | —CH₂—C(Cl)=CH₂ | H | |
| 2.012 | —CH₂CH₂CH₂F | H | |
| 2.013 | —CH₂CH₂CH₂F | 6-CH₃ | |
| 2.014 | —CH₂CH₂CH₂F | 6-OCH₃ | |
| 2.015 | —CH₂CH₂CH₂F | 6-F | |
| 2.016 | —CH(CH₃)CH₂F | 6-F | |
| 2.017 | —CH(CH₃)CH₂F | 6-CH₃ | |
| 2.018 | —CH(CH₂F)C₂H₅ | H | |
| 2.019 | —CH(CH₂F)C₂H₅ | 6-CH₃ | |
| 2.020 | —CH(CH₂F)CH₂F | H | |
| 2.021 | —CH(CH₂F)CH₂F | 6-CH₃ | |
| 2.022 | —CH₂CH=CHCl (E) | 6-OCHF₂ | |
| 2.023 | —CH₂CH=CHCl (E) | 5-CH₃ | |
| 2.024 | —CH₂CH=CHCl (E) | 4-CH₃ | |
| 2.025 | —CH₂CH=CH—CF₃ | H | |
| 2.026 | —CH₂CH=CHBr | H | +188 to +190 |
| 2.027 | —CH₂CH=CHBr | 6-CH₃ | |
| 2.028 | —CH₂CH=CHBr | 6-OCH₃ | |
| 2.029 | —CH₂CH=CHBr | 5-CH₃ | |
| 2.030 | —CH₂CH=CHBr | 4-CH₃ | |
| 2.031 | —CH₂-(cyclohex-3-enyl) | H | |
| 2.032 | —CH₂-(cyclohex-3-enyl) | 6-CH₃ | |
| 2.033 | —CH₂-(cyclohex-3-enyl) | 6-OCH₃ | |
| 2.034 | —CH₂-(cyclohex-3-enyl) | 5-CH₃ | |
| 2.035 | cyclohex-2-enyl | H | |
| 2.036 | cyclohex-2-enyl | 6-CH₃ | |
| 2.037 | cyclohex-2-enyl | 6-OCH₃ | |
| 2.038 | cyclohex-2-enyl | 6-OCHF₂ | |
| 2.039 | cyclohex-2-enyl | 5-CH₃ | |
| 2.040 | cyclohex-2-enyl | 4-CH₃ | |

TABLE 2-continued (II)

Structure: Pyridine with R₁, SO₂-A, SO₂NH₂ substituents

| No. | A | R₁ | Melting point [°C.] |
|---|---|---|---|
| 2.041 | oxetanyl | H | |
| 2.042 | oxetanyl | 6-CH₃ | |
| 2.043 | oxetanyl | 6-OCH₃ | |
| 2.044 | oxetanyl | 5-Cl | |
| 2.045 | oxetanyl | 5-CH₃ | |
| 2.046 | tetrahydrofuranyl | H | |
| 2.047 | tetrahydrofuranyl | 6-CH₃ | |
| 2.048 | tetrahydrofuranyl | 6-OCH₃ | |
| 2.049 | tetrahydrofuranyl | 6-OCHF₂ | |
| 2.050 | −CH₂−oxetanyl | H | |
| 2.051 | −CH₂−oxetanyl | 6-CH₃ | |
| 2.052 | −CH₂−oxetanyl | 6-OCH₃ | |
| 2.053 | −CH₂−oxetanyl | 6-OCHF₂ | |
| 2.054 | −CH₂−tetrahydrofuranyl | H | |
| 2.055 | −CH₂−tetrahydrofuranyl | 6-CH₃ | |
| 2.056 | −CH₂−tetrahydrofuranyl | 6-OCH₃ | |
| 2.057 | −CH₂−tetrahydropyranyl | H | |
| 2.058 | −CH₂−tetrahydropyranyl | 6-CH₃ | |
| 2.059 | −CH₂−tetrahydropyranyl | 6-OCH₃ | |
| 2.060 | −CH₂−tetrahydropyranyl | 6-OCHF₂ | |
| 2.061 | thietanyl-SO₂ | H | |
| 2.062 | thietanyl-SO₂ | 6-CH₃ | |
| 2.063 | thietanyl-SO₂ | 6-OCH₃ | |
| 2.064 | thietanyl-SO₂ | 5-CH₃ | |
| 2.065 | tetrahydrothiophenyl-SO₂ | H | |
| 2.066 | tetrahydrothiophenyl-SO₂ | 6-CH₃ | |

TABLE 2-continued $$\text{(II)}$$

Structure: R₁-substituted pyridine with SO₂—A and SO₂NH₂ groups

| No. | A | R₁ | Melting point [°C.] |
|---|---|---|---|
| 2.067 | tetrahydrothiophene-SO₂ (ring) | 6-OCH₃ | |
| 2.068 | —CH₂—(tetrahydrothiophene-SO₂) | H | |
| 2.069 | —CH₂—(tetrahydrothiophene-SO₂) | 6-CH₃ | |
| 2.070 | —CH₂—(tetrahydrothiophene-SO₂) | 6-OCH₃ | |
| 2.071 | —(N-CH₃ piperidine) | H | |
| 2.072 | —(N-CH₃ piperidine) | 6-CH₃ | |
| 2.073 | —(N-CH₃ piperidine) | 6-OCH₃ | |
| 2.074 | —CH₂—CBr=CH₂ | H | +158 to +159 |
| 2.075 | —CH₂—CCl=CH₂ | H | +172 to +173 |
| 2.076 | —CH₂CH=CHCl (Z) | H | +196 to +197 |
| 2.077 | —CH₂CH=CHCl (Z) | 6-CH₃ | |
| 2.078 | —CH₂CH=CHCl (Z) | 6-OCH₃ | |
| 2.079 | —CHCH₂OCH₃ (with CH₃) | H | +232 to +234 |
| 2.080 | —CHCH₂OCH₃ (with CH₃) | 6-CH₃ | |
| 2.081 | —CH₂CH₂SO₂CH₃ | H | +105 to +110 |
| 2.082 | —CHCH₂Cl (with CH₃) | H | +185 to +188 |
| 2.083 | —CH₂CH₂CH₂Cl | H | +194 to +195 |
| 2.084 | —CH₂CH₂CH₂Cl | 6-CH₃ | |
| 2.085 | —CH₂CH₂CH₂Cl | 6-OCH₃ | |
| 2.086 | —CHF₂ | H | |
| 2.087 | —CF₂CHF₂ | H | |
| 2.088 | —CH₂CH₂N(CH₃)₂ | H | |
| 2.089 | —CH₂CH₂N(C₂H₅)₂ | H | |
| 2.090 | —CH₂CH₂NHCH₃ | H | |
| 2.091 | —CH₂CH₂NHCH₃ | 6-CH₃ | |
| 2.092 | —CH₂CH₂N(CH₃)₂ | 6-CH₃ | |
| 2.093 | —CH₂CH=CH₂ | 6-OCH₃ | |
| 2.094 | —CH₂CH=CH₂ | 6-OCHF₂ | |
| 2.095 | —CH₂C≡CH | H | +164 to +165 |
| 2.096 | —CH₂C≡CH | 6-CH₃ | |
| 2.097 | —CH₂C≡CH | 6-OCH₃ | |
| 2.098 | —CH₂CF=CHCH₃ | H | +116 to +118 (decomp.) |
| 2.099 | —CH₂CH₂CH=CH₂ | H | |
| 2.100 | —CH₂CH₂CH=CH₂ | 6-CH₃ | |
| 2.101 | —CH₂CH₂CH=CH₂ | 6-OCH₃ | |
| 2.102 | —CH₂CH₂CH=CH₂ | 5-CH₃ | |
| 2.103 | —CH₂CH₂CH=CH₂ | 4-CH₃ | |
| 2.104 | —CH(CH₃)CH=CH₂ | H | +176 (decomp.) |
| 2.105 | —CH(CH₃)CH=CH₂ | 6-CH₃ | |
| 2.106 | —CH(CH₃)CH=CH₂ | 6-OCH₃ | |
| 2.107 | —CH(CH₃)CH=CH₂ | 5-CH₃ | |
| 2.108 | —CH(CH₃)CH=CH₂ | 5-Cl | |
| 2.109 | —CH(CH₃)CH=CH₂ | 5-CH₃ | |
| 2.110 | —CH₂CH=CHCH₃ | H | |
| 2.111 | —CH₂CH=CHCH₃ | 6-CH₃ | |
| 2.112 | —CH₂CH=CHCH₃ | 6-OCH₃ | |
| 2.113 | —CH₂CH=CHCH₃ | 5-CH₃ | |
| 2.114 | —CH₂CH=CHCH₃ | 4-CH₃ | |
| 2.115 | —CH₂C≡C—CH₃ | H | |
| 2.116 | —CH₂C≡C—CH₃ | 6-CH₃ | |
| 2.117 | —CH₂C≡C—CH₃ | 6-OCH₃ | |
| 2.118 | —CH₂C≡C—CH₃ | 6-OCHF₂ | |
| 2.119 | —CH₂C≡C—CH₃ | 5-CH₃ | |
| 2.120 | —CH₂C≡C—CH₃ | 5-Cl | |
| 2.121 | —CH₂C≡C—CH₃ | 4-CH₃ | |
| 2.122 | —CH₂CH₂C≡CH | H | |
| 2.123 | —CH₂CH₂C≡CH | 6-CH₃ | |
| 2.124 | —CH₂CH₂C≡CH | 6-OCH₃ | |
| 2.125 | —CH₂CH₂C≡CH | 6-OCHF₂ | |
| 2.126 | —CH₂CH₂C≡CH | 5-CH₃ | |
| 2.127 | —CH₂CH₂C≡CH | 4-CH₃ | |
| 2.128 | —CH₂CH=CHCl (E) | H | +230 (decomp.) |
| 2.129 | —CH₂CH=CHCl (E) | 6-CH₃ | |
| 2.130 | —CH₂CH=CHCl (E) | 6-OCH₃ | |
| 2.131 | —CH₂CH=CHCl (Z) | 6-OCHF₂ | |
| 2.132 | —CH₂CH=CHCl (Z) | 5-CH₃ | |
| 2.133 | —CH₂CH=CHCl (Z) | 5-Cl | |
| 2.134 | —CH₂CH=CHCl (Z) | 4-CH₃ | |

TABLE 3

$$\text{Structure: R}_1\text{-pyridine with Q and SO}_2\text{NH}_2$$

| No. | R₁ | Q | Melting point [°C.] |
|---|---|---|---|
| 3.001 | H | F | +121 to +123 |
| 3.002 | 5-Cl | F | +119 to +122 |
| 3.003 | 5-CH₃ | F | |
| 3.004 | 6-F | F | |
| 3.005 | 6-CH₃ | F | |
| 3.006 | 6-OCH₃ | F | |
| 3.007 | 4-CH₃ | F | |
| 3.008 | H | SH | +102 to +104 |
| 3.009 | 6-CH₃ | SH | |
| 3.010 | 6-OCHF₂ | F | |
| 3.011 | 6-OCHF₂ | SH | |

BIOLOGICAL EXAMPLES

Example B1: Herbicidal action, pre-emergence

In a greenhouse, the test plants are sown in seed dishes, and immediately afterwards the soil surface is treated with an aqueous spray liquor, corresponding to an application rate of 4 kg of active compound/ha. The seed dishes are kept in the greenhouse at 22°–25° C. and 50–70% relative atmospheric humidity.

After 3 weeks, the herbicidal action is assessed using a scoring scale from 1 to 9 (1=complete damage, 9=no action) in comparison with an untreated control group.

Scores from 1 to 4 (in particular 1 to 3) suggest a good to very good herbicidal action. Scores from 6 to 9 (in particular from 7 to 9) suggest a good tolerance (in particular in crop plants).

In this test, the compounds of Table 1 have a powerful herbicidal action.

Example B2: Herbicidal action, post-emergence (contact herbicide)

A number of monocotyledon and dicotyledon weeds were sprayed after emergence (in the 4- to 6-leaf stage) with an aqueous dispersion of active substance at a dosage rate of 4 kg of active compound per hectare, applied to the plants, and the latter were kept at 24°–26° C. and 45–60% relative atmospheric humidity. 15 days after the treatment, the experiment is evaluated. In this test too, the compounds of Table 1 have a good herbicidal action.

Example B3: Herbicidal action for paddy rice

The water weed *Echinochloa crus galli* and *Monocharia vag.* are sown in plastic beakers (surface: 60 cm$^2$, volume: 500 ml). After sowing, the beakers are filled with water up to the surface of the soil. 3 days after sowing, more water is added until the water level is slightly above the soil surface (3–5 ram). The application is effected 3 days after sowing by spraying the test substances onto the containers. The dosage rate used corresponds to an amount of active substance of 4 kg of active ingredient per hectare. The beakers with the plants are then placed in the greenhouse under optimum growth conditions for the rice weeds, i.e. at 25°–30° C. and high atmospheric humidity.

The experiments are evaluated 3 weeks after the application. The compounds of Table 1 damage the weeds in these experiments, but not the rice.

Example B4: Growth inhibition in tropical cover crops

The test plants *Centrosema pubescens* and *Psophocarpus palustris* are propagated by cuttings in 4 cm peat pots filled with terrestrial soil (45%), peat (45%) and zonolite (10 They are grown in the greenhouse at a daytime temperature of 27° C. and a night temperature of 23° C. The photoperiod is at least 14 hours/day at an intensity of at least 7000 lux.

Approx. 50 days after the cuttings have been planted, they are repotted into 13 cm pots, 4–5 plants/pot. After a further 60 days, the plants are cut back to approx. 15 cm in height, and the application is effected. For this purpose, they are sprayed with 0.1 to 300 g of active substance/ha (usually as a 25% formulation) in an aqueous spray liquor. The water application rate is approx. 200 /l ha.

4 weeks after the application, the weight of the additional growth is determined and given as a percentage of the average of the untreated controls. The necrotic lesions are given as a percentage of the total leaf area.

It emerges that the additional growth of the treated plants is markedly less than that of the untreated controls.

Example B5: Growth regulation of soya beans

Test plants cv. Williams are sown in 11 cm clay pots filled with terrestrial soil (45%), peat (45%) and zonolite (10%) and grown in a growth cabinet at a daytime temperature of 24° C. and a night temperature of 19° C. The photoperiod is 16 hours per day at an intensity of approx. 350 micro-Einstein.

Approx. 24 days after sowing, they are repotted into 18 cm pots, 2 plants/pot. After a further 12 days and when the plants have produced 5–6 trifoliate leaves, the application is effected using 0.1 to 300 g of active substance/ha, generally in a 25% formulation and in an aqueous spray liquor. The water application rate is approx. 200 /l ha.

The evaluation takes place approx. 4 weeks after the application. For this purpose, the height of the additional growth is measured and given as a percentage of the average of the untreated controls. The necrotic lesions are represented as a percentage of the total leaf area.

The treated plants show markedly less additional growth than the untreated controls.

Example B6: Growth inhibition in cereals

Test plants (spring barley cv. Iban) are sown in 15 cm plastic pots filled with sterile terrestrial soil and grown in a growth cabinet at a daytime temperature of 10°–15° C. and a night temperature of 5°–10° C. The photoperiod is 13.5 hours per day at an intensity of approx. 25,000 lux.

Approx. 34 days after sowing and thinning to 4 plants/pot, the application is effected using 0.1 to 300 g of active substance/ha, usually in a 25% formulation and in an aqueous spray liquor. The water application rate is approx. 500 l/ha. After the application, the plants are placed in a greenhouse at a daytime temperature of at least 10° C. The photoperiod is at least 13.5 hours/day.

The evaluation takes place approximately 28 days after the treatment. For this purpose, the height of the additional growth is given as a percentage of the average of the untreated controls. The necrotic lesions am represented as a percentage of the total leaf area.

Compared with untreated controls, the treated plants show a reduced additional growth.

Example B7: Growth inhibition in grasses

A grass mixture (for example Poa, Festuca, Lolium, Bromus, Cynosurus) and clover (Trifolium pratense/-repens) are sown in 15 cm plastic pots filled with sterile terrestrial soil and grown in a greenhouse at a daytime temperature of 21 ° C. and a night temperature of 17° C. The photoperiod is 13.5 hours/day at a light intensity of at least 7000 lux. After the emergence, the plants are cut back weekly to a height of approx. 6 cm. Approx. 42 days after sowing and 1 day after the last cut, the application is effected using 0.1 to 300 g of active substance/ha, usually in a 25% formulation and in an aqueous spray liquor. The water application rate is approx. 500 l/ha.

The evaluation takes place approx. 3 weeks after the treatment. For this purpose, the height of the additional growth is measured and given as a percentage of the average of the untreated controls. The necrotic lesions are represented as a percentage of the total leaf area.

What is claimed is:

1. An N-pyridinesulfonyl-N'-pyrimidinyl- or -triazinylurea of the formula I

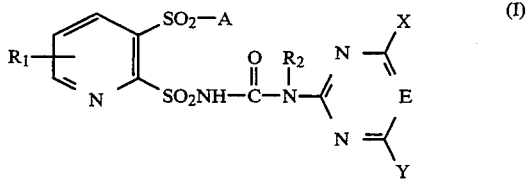

in which $R_1$ is hydrogen, halogen, $C_1$-$C_4$alkyl, $C_1$-$C_4$alkoxy, $C_1$-$C_4$alkylthio, $C_1$-$C_4$haloalkoxy or $CF_3$; $R_2$ is hydrogen or $C_1$-$C_4$alkyl; A is $C_1$-$C_4$alkyl which is substituted by $C_2$-$C_4$alkenyl, it being possible for the $C_2$-$C_4$alkenyl radical to be additionally monosubstituted to trisubstituted by halogen; X is $C_1$-$C_3$alkoxy or $C_1$-$C_3$alkoxy which is monosubstituted to trisubstituted by halogen; Y is halogen, $C_1$-$C_3$alkoxy, $C_1$-$C_3$alkoxy which is monosubstituted to trisubstituted by halogen, or is cyclopropyl; and E is nitrogen or the methine group, or a salt thereof.

2. A compound according to claim 1, wherein $R_1$ is hydrogen, halogen, $C_1$-$C_4$alkyl, $C_1$-$C_4$alkoxy, $C_1$-$C_4$alkylthio or $CF_3$.

3. A compound according to claim 1, wherein $R_2$ is hydrogen.

4. A compound according to claim 1, wherein Y is chlorine, $C_1$-$C_3$alkoxy or $C_1$-$C_3$alkoxy which is monosubstituted to trisubstituted by halogen.

5. A compound of the formula I according to claim 1, wherein X is methoxy, ethoxy or difluoromethoxy; and Y is methoxy, ethoxy, difluoromethoxy or chlorine.

6. A compound of the formula I according to claim 1, wherein X is methoxy or ethoxy; and Y is methoxy.

7. A compound of the formula I according to claim 1, wherein E is the methine bridge.

8. A compound of the formula I according to claim 1, wherein $R_1$ is hydrogen, methyl, methoxy, fluorine or chlorine.

9. A compound of the formula I according to claim 1, wherein $R_1$ and $R_2$ are hydrogen.

10. A compound of the formula I according to claim 1 wherein A is allyl, methallyl, 2-methylpropenyl or 3-chloroallyl.

11. A compound of the formula I according to claim 10, wherein $R_1$ and $R_2$ are hydrogen.

12. A compound of the formula I according to claim 1, wherein $R_1$ is hydrogen, halogen, $C_1$-$C_2$alkyl, $C_1$-$C_2$alkoxy, $C_1$-$C_2$alkylthio, $C_1$-$C_2$-haloalkoxy or $CF_3$; $R_2$ is hydrogen or $C_1$-$C_2$alkyl; A is $C_1$-$C_2$alkyl which is substituted by $C_2$-$C_3$alkenyl, it being possible for the $C_2$-$C_3$alkenyl radical to be additionally monosubstituted to trisubstituted by halogen; X is $C_1$-$C_2$alkoxy or $C_1$-$C_2$alkoxy which is monosubstituted to trisubstituted by halogen; Y is halogen, $C_1$-$C_2$alkoxy, $C_1$-$C_2$alkoxy which is monosubstitued to trisubstituted by halogen, or is cyclopropyl.

13. A compound of the formula I according to claim 12, wherein $R_1$ is hydrogen, halogen, $C_1$-$C_2$alkyl, $C_1$-$C_2$alkylthio or $CF_3$.

14. A compound of the formula I according to claim 1, wherein $R_1$ and $R_2$ are hydrogen and A is $C_1$-$C_2$alkyl which is substituted by $C_2$-$C_4$alkenyl, it being possible for the $C_2$-$C_4$alkenyl radical to be additionally monosubstituted to trisubstituted by fluorine or chlorine.

15. A compound according to claim 11, wherein A is allyl, methallyl or 3-chloroallyll; X is methoxy, ethoxy or difluoromethoxy and Y is methoxy, ethoxy, difluoromethoxy or chlorine.

16. N-(3-Allylsulfonylpyridin-2-ylsulfonyl)N'-(4,6-dimethoxypyrimidin-2-yl)urea.

17. A herbicidal and growth-inhibiting composition, which contains at least an effective amount of a sulfonylurea of the formula I, according to claim 1 and a carrier therefor.

18. A method for controlling undesired plant growth, wherein an active substance of the formula I, according to claim 1, or a composition containing this active substance, is applied in an effective amount to the plants or their environment.

19. A method according to claim 18, wherein an amount of active substance of between 0.001 and 5 kg per hectare is applied.

20. A method for inhibiting plant growth, wherein an active substance of the formula I, according to claim 1, or a composition containing this active substance, is applied in an effective amount to the plants or their environment.

21. A method for influencing plant growth with the purpose of increasing the yield, wherein an active substance of the formula I, according to claim 1, or a composition containing this active substance, is applied in an effective amount to the plants or their environment.

22. A method according to claim 18 for selective weed control in crops, either pre- or post-emergence.

23. A composition according to claim 17 wherein the sulfonylurea comprises between 0.1% and 95% of the mixture.

* * * * *